US011992478B2

(12) United States Patent
Ridky et al.

(10) Patent No.: US 11,992,478 B2
(45) Date of Patent: May 28, 2024

(54) METHODS OF USING ANDROGEN RECEPTOR INHIBITORS AS CANCER THERAPEUTICS

(71) Applicant: THE TRUSTEES OF THE UNIVERSITY OF PENNSYLVANIA, Philadelphia, PA (US)

(72) Inventors: Todd Ridky, Bryn Mawr, PA (US); Christopher Natale, Philadelphia, PA (US); Cristina Aguirre Portoles, Philadelphia, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 249 days.

(21) Appl. No.: 17/179,801

(22) Filed: Feb. 19, 2021

(65) Prior Publication Data
US 2021/0251966 A1 Aug. 19, 2021

Related U.S. Application Data

(60) Provisional application No. 62/978,719, filed on Feb. 19, 2020.

(51) Int. Cl.
| | |
|---|---|
| *A61K 31/4164* | (2006.01) |
| *A61K 31/09* | (2006.01) |
| *A61K 31/122* | (2006.01) |
| *A61K 31/131* | (2006.01) |
| *A61K 31/167* | (2006.01) |
| *A61K 31/21* | (2006.01) |
| *A61K 31/277* | (2006.01) |
| *A61K 31/4155* | (2006.01) |
| *A61K 31/4166* | (2006.01) |
| *A61K 31/4439* | (2006.01) |
| *A61K 45/06* | (2006.01) |

(52) U.S. Cl.
CPC ........ *A61K 31/4164* (2013.01); *A61K 31/122* (2013.01); *A61K 31/131* (2013.01); *A61K 31/21* (2013.01); *A61K 31/4155* (2013.01); *A61K 45/06* (2013.01)

(58) Field of Classification Search
CPC .............. A61K 31/4164; A61K 31/122; A61K 31/131; A61K 31/21; A61K 31/4155; A61K 31/09; A61K 31/167; A61K 31/277; A61K 31/4166; A61K 31/4439; A61K 45/06; A61K 2300/00
See application file for complete search history.

(56) References Cited

U.S. PATENT DOCUMENTS

2019/0375732 A1* 12/2019 Hung .................. A61K 47/545

FOREIGN PATENT DOCUMENTS

WO   WO-2013067142 A1 *  5/2013  ........... C07D 233/86

OTHER PUBLICATIONS

Berg, A. Hakan, et al. "Identification and characterization of membrane androgen receptors in the ZIP9 zinc transporter subfamily: I. Discovery in female atlantic croaker and evidence ZIP9 mediates testosterone-induced apoptosis of ovarian follicle cells." Endocrinology 155.11 (2014): 4237-4249.
Beyersmann, Detmar, and Hajo Haase. "Functions of zinc in signaling, proliferation and differentiation of mammalian cells." Biometals 14.3 (2001): 331-341. (Abstract).
Bulldan, Ahmed, et al. "Testosterone/bicalutamide antagonism at the predicted extracellular androgen binding site of ZIP9." Biochimica et Biophysica Acta (BBA)-Molecular Cell Research 1864.12 (2017): 2402-2414.
Chesters, John K., Linda Petrie, and Kenneth E. Lipson. "Two zinc-dependent steps during G1 to S phase transition." Journal of cellular physiology 155.3 (1993): 445-451. (Abstract).
Cockshott, Ian D. "Bicalutamide." Clinical pharmacokinetics 43.13 (2004): 855-878. (Abstract).
Masiello, David, et al. "Bicalutamide functions as an androgen receptor antagonist by assembly of a transcriptionally inactive receptor." Journal of Biological Chemistry 277.29 (2002): 26321-26326.
Osguthorpe, D. J., and A. T. Hagler. "Mechanism of androgen receptor antagonism by bicalutamide in the treatment of prostate cancer." Biochemistry 50.19 (2011): 4105-4113.
Schweizer, Michael T., and Evan Y. Yu. "AR-signaling in human malignancies: prostate cancer and beyond." Cancers 9.1 (2017): 7.
Taniguchi, Masanari, et al. "Essential role of the zinc transporter ZIP9/SLC39A9 in regulating the activations of Akt and Erk in B-cell receptor signaling pathway in DT40 cells." PloS one 8.3 (2013): e58022.
Thomas, Peter, Aubrey Converse, and Håkan A. Berg. "ZIP9, a novel membrane androgen receptor and zinc transporter protein." General and comparative endocrinology 257 (2018): 130-136.
Thomas, Peter, Yefei Pang, and Jing Dong. "Membrane androgen receptor characteristics of human ZIP9 (SLC39A) zinc transporter in prostate cancer cells: Androgen-specific activation and involvement of an inhibitory G protein in zinc and MAP kinase signaling." Molecular and cellular endocrinology 447 (2017): 23-34.

* cited by examiner

*Primary Examiner* — Joseph R Kosack
*Assistant Examiner* — Sagar Patel
(74) *Attorney, Agent, or Firm* — Saul Ewing LLP; Domingos J. Silva

(57) ABSTRACT

Provided herein are methods of treating cancer in a subject with a ZIP9 inhibitor. In certain embodiments, the cancerous tissues do not express the nuclear androgen receptor (AR). These methods, alone or in combination with other cancer therapies, can improve treatment outcomes in patients suffering from cancer, particularly male patients.

25 Claims, 13 Drawing Sheets

A  B

A
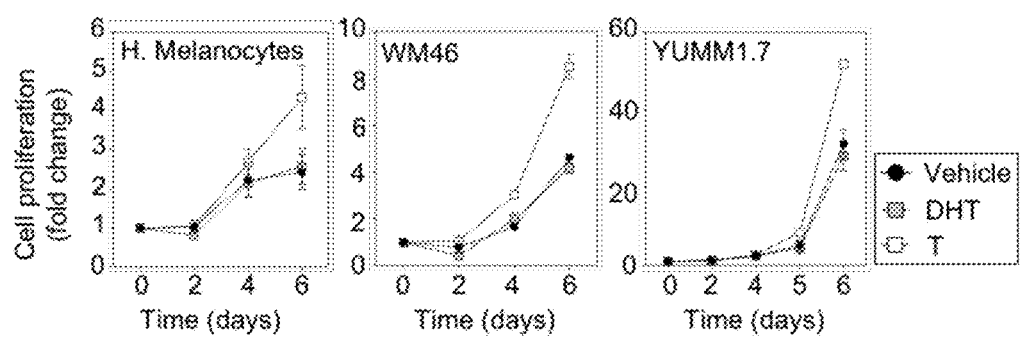
B
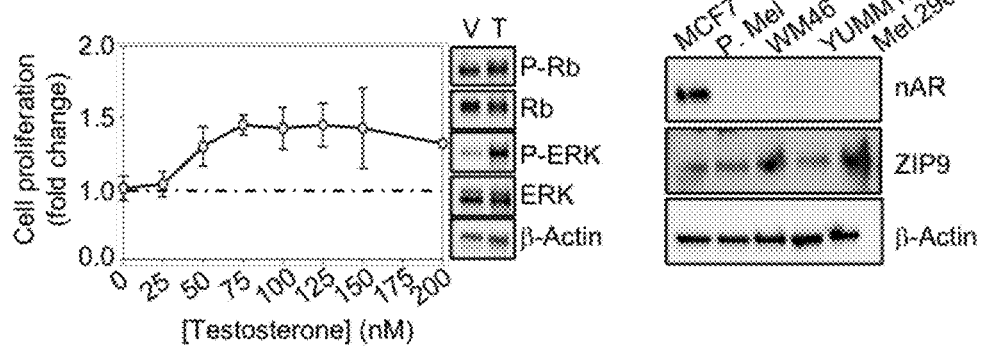
C
FIGs. 3A-3C

METHODS OF USING ANDROGEN RECEPTOR INHIBITORS AS CANCER THERAPEUTICS

CROSS-REFERENCE TO RELATED APPLICATION

This application claims priority to U.S. Provisional Patent Application Ser. No. 62/978,719 entitled "METHODS OF USING ANDROGEN RECEPTOR INHIBITORS AS CANCER THERAPEUTICS," filed Feb. 19, 2020, the disclosure of which is incorporated herein by reference in its entirety.

BACKGROUND OF THE INVENTION

Cancer is still one of the deadliest threats to human health. In 2012, there were 14 million new cases of cancer worldwide and 8.2 million cancer-related deaths. The number of new cancer cases is expected to rise to 22 million by 2030, and worldwide cancer deaths are projected to increase by 60%. Despite the latest advances in targeted and immune therapies most patients with metastatic cancer die from their cancer, and there is acute need for identification of new cancer targets, and effective agents to safely engage them.

For most cancer types, incidence and mortality are higher in males than in females. In the U.S., males are 15% are more likely to develop cancer, and 40% more likely to die of this disease than females. These sex differences are observed in the majority of cancer types from non-reproductive tissues, and remain even after controlling for known risk factors such as environmental and occupational exposures. Although this sex difference has been appreciated for at least 75 years, the mechanism(s) responsible are only now emerging.

There is thus a need for novel compositions and methods for treating, ameliorating, and/or preventing cancer. The present invention addresses this need.

BRIEF SUMMARY OF THE INVENTION

In various embodiments, a method of treating cancer is provided. The method includes administering to a subject in need thereof a composition comprising a therapeutically effective amount of at least one active agent that inhibits ZIP8, and wherein the cancer is not androgen receptor (AR)-dependent.

In various embodiments, method of treating cancer includes identifying a subject suffering from cancer that has failed at least one prior cancer therapy, wherein the cancer is not androgen receptor (AR)-dependent; and administering to the subject a composition comprising a therapeutically effective amount of at least one active agent that inhibits ZIP9.

In various embodiments, a method of reducing proliferation of cells in a cancerous tumor is provided. The method includes contacting cells in the cancerous tumor with at least one active agent that inhibits ZIP9; and reducing the proliferation of cells in the cancerous tumor, wherein the cancerous tumor is not androgen receptor (AR)-dependent; and wherein the cancerous tumor is not prostate cancer or testicular cancer.

In various embodiments, the method surprisingly and advantageously results in tumor proliferation being selectively reduced in a male subject compared to a female subject.

BRIEF DESCRIPTION OF THE FIGURES

The drawings illustrate generally, by way of example, but not by way of limitation, various embodiments of the present application.

FIG. 2A: Murine melanoma (YUMM1.7) tumors grow faster in C57BL/6 males compared to females. FIG. 2B: Human melanoma (WM46) tumors grow faster in immunodeficient SCID male mice. Five mice were used per condition. Error bars represent standard error of the mean (SEM).

FIGS. 3A-3C show that testosterone promotes proliferation of primary human melanocytes (H. Melanocytes), human melanoma cells (WM46) and mouse melanoma cells (YUMA/11.7). FIG. 3A: Cell proliferation in melanoma cells and melanocytes treated with Testosterone (T) or dihydrotestosterone (DHT). FIG. 3B: Testosterone increases proliferation of WM46 cells in a dose dependent manner reaching a maximum response at 75 nM. The graph represents the average of three independent experiments. Testosterone increases ERK phosphorylation. Error bars=SEM. FIG. 3C: Western blot, Human primary melanocytes (H. Mel), human melanoma (WM46), murine melanoma (YUMM1.7) and human ocular melanoma (Mel.290) do not express the classical nuclear androgen receptor nAR. MCF7 breast cells were used as positive control for nAR expression. In contrast, each of these cell types expresses ZIP9.

FIG. 4A: Time course analysis of $Zn^{++}$ influx upon addition of T. Fluo-Zin3 was used as $Zn^{++}$ reporter. FIG. 4B: Intracellular $Zn^{++}$ increases following 48 hours of exposure to testosterone. FIG. 4C: Zinc chelator inhibits the pro-proliferative effects of testosterone. Cell proliferation was determined over 6-days. FIG. 4D: Proliferation of WM46 melanoma cells was determined following addition of medically relevant cations including zinc, iron, and manganese. Only zinc promoted proliferation was determined over 6-days.

FIG. 5A illustrates the validation of ZIP9 [(SLC39A9 Antibody (PAS-52485)] and androgen receptor [(Leica AR-318-L-CE, clone AR27 (clone AR27, 1:25)] antibodies for immunohistochemistry. ZIP9 staining performed in wild-type and ZIP9 knock-out cells. Prostate gland tissue and human prostate cancer samples were used as positive controls for AR. Representative images of human melanoma samples stained for ZIP9 and AR. Tumors expressing low, medium and high levels of ZIP9 are shown. Replicates from the same samples stained for AR are shown. 20× magnification (1.6× zoom). Scale bar=60 µM. G. FIG. 5B is a graphic representation of the % of tumors that express ZIP9. Data from nevus, primary melanomas and metastatic melanoma are displayed. FIG. 5C is a graphic representation of the percentage of nevi, primary lesions and metastatic tumors classified according to ZIP9 intensity (Score 1=1-25%, 2=26-50%, 3=51-75%, 4=76-100%).

FIG. 7A shows that ZIP9 depletion (ΔZIP9) inhibits MAPK signaling. FIG. 7B shows that testosterone promotes proliferation of WT human (WM46) and mouse (YUMM) melanoma cells, but has no effect on isogenic clones lacking ZIP9. Testosterone stimulated proliferation requires zinc cation, as testosterone effects are blocked by the zinc chelator TPEN. FIG. 7C: Testosterone induces zinc influx in WT WM46 cells, but has no no significant effect on zinc in WM46 cells lacking ZIP9 (ΔZIP9). FIG. 7D shows that subcutaneous melanoma derived from ΔZIP9 WM46 grows significantly slower in male mice than tumors derived from isogenic wtZIP9 WM46. There is no significant difference in tumor growth between wtZIP9 WM46 and ΔZIP9 WM46 melanoma in female mice. ****p-value<0.001. *p-value<0.05; p-value<0.01; *p-value<0.001.

FIG. 9A shows that a mouse PDAC (mPDAC) grows faster in male vs. female mice. FIG. 9B shows a Western blot for nAR and ZIP9 in cell lysates from breast cancer (MCF7, positive control), human PDAC (hPANC, MiaPaca, HPAC), and mPDAC. FIG. 9C shows that testosterone, but not dihydrotestosterone, promotes proliferation in human and murine PDAC. FIG. 9D is a Western blot showing ZIP9 protein in parental WT 2838mPDAC, and absence of ZIP9 protein in an isogenic2838 clone with CRISPR-CAS9 mediated ZIP9/SLC39A9 gene ablation (ΔZIP9). FIG. 9E shows that mPDAC ΔZIP9 cells do not respond to testosterone in vitro.

FIG. 10A shows that 2 μM Bicalutamide (BIC) and 3 μM Enzalutamide (ENZ) each completely block testosterone-induced hyperproliferation while having no effect on cell proliferation in the absence of testosterone. FIG. 10B shows that testosterone-induced ERK activation is blocked by BIC or by the Zn' chelator TPEN. FIG. 10C shows that different murine and human melanoma cells all respond to testosterone and to bicalutamide. FIG. 10D shows that bicalutamide prevents the testosterone-dependent Zinc influx in WM46 cells. FIG. 10E shows that FDA-approved flutamide derivatives (BIC, ENZ, and apalutamide (APA)) each inhibit testosterone driven increased proliferation in WM46 human melanoma cells.

FIG. 12A shows down-regulated proteins in black. FIG. 12B is a Western blot showing that testosterone promotes YAP nuclear translocation in WM46 cells. I3-Actin is used as control for the cytosolic fraction; PARP is used as a control for the nuclear fraction.

FIG. 13A shows that systemic daily delivery of bicalutamide (30 mg/kg/day) inhibits tumor growth in male SCID mice, but does not affect growth of WM46 in female mice. FIG. 13B shows that male mice bearing ΔZIP9 tumors do not respond to bicalutamide treatment. FIG. 13C shows that systemic daily delivery of apalutamide (APA) (20 mg/kg/day) inhibits tumor growth and extend survival in male SCID mice.

DETAILED DESCRIPTION OF THE INVENTION

Figure 1:
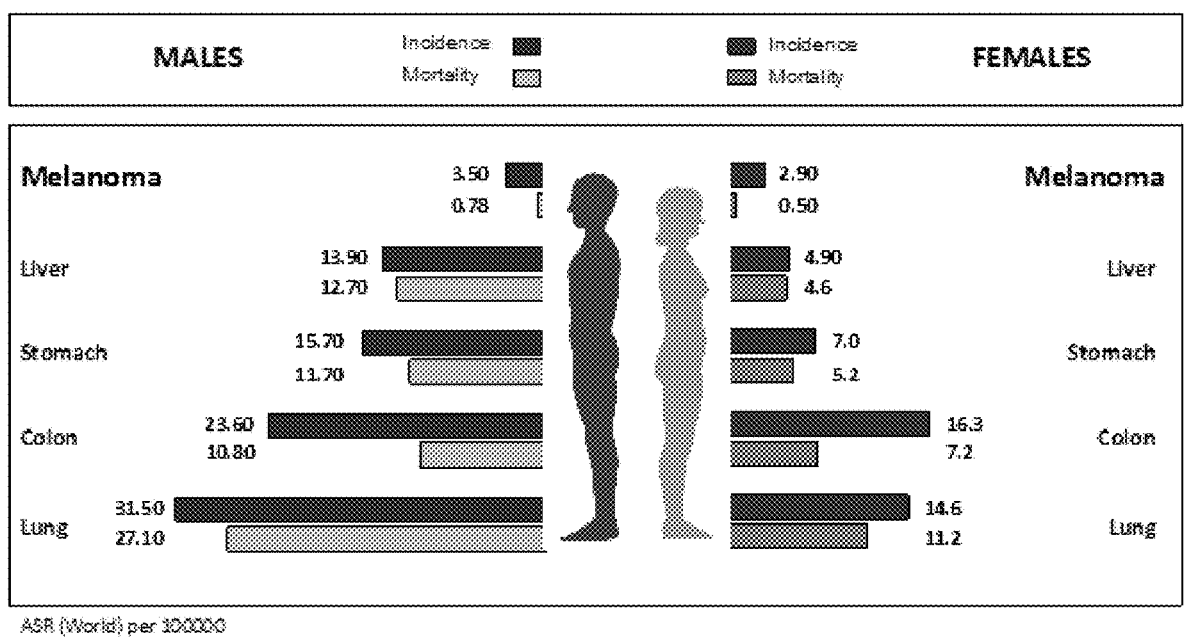
FIG. 1 shows that for most common cancer types worldwide, incidence and mortality rates are higher in males than females. Age standardized rates are shown for the most common cancers initiating in non-reproductive tissues.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

DEFINITIONS

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

As used herein, the term "composition" or "pharmaceutical composition" refers to a mixture of at least one compound described herein with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect (Emax) achieved within an assay.

As used herein, the terms "inhibitor of AR," "inhibits AR," or "AR inhibitor" are synonymous and mean a substance that binds to AR and prevents its normal biological activity, including any part of AR's transcriptional regulatory functions. In certain embodiments, the AR inhibitor prevents binding of AR to DNA. AR inhibitors include AR antagonists, and the term "inhibitor" and "antagonist" are used interchangeably herein.

As used herein, the terms "inhibitor of ZIP9," "inhibits ZIP9," or "ZIP inhibitor" are synonymous and mean a substance that binds to ZIP9 and prevents its normal biological activity. The ZIP9 inhibitor can prevent binding of testosterone to ZIP9, or prevent the activation of ZIP9 by testosterone. The ZIP9 inhibitor can reduce downstream zinc-dependent protein signaling, including YAP and MAPK signaling.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids or bases, including inorganic acids or bases, organic acids or bases, solvates, hydrates, or clathrates thereof.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds described herein include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "pharmaceutically acceptable carrier" or "pharmaceutically acceptable excipient" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound described herein within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound(s) described herein, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound(s) described herein, and are physiologically acceptable to the patient. Supplementary active compounds may also be incorporated into the compositions. The "pharmaceutically acceptable carrier" may further include a pharmaceutically acceptable salt of the compound(s) described herein. Other additional ingredients that may be included in the pharmaceutical compositions used with the methods or compounds described herein are known in the art and described, for example in Remington's Pharmaceutical Sciences (Genaro, Ed., Mack Publishing Co., 1985, Easton, PA), which is incorporated herein by reference.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "potency" refers to the dose needed to produce half the maximal response ($ED_{50}$).

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound or compounds as described herein (alone or in combination with another pharmaceutical agent), to a patient, or application or administration of a therapeutic agent to an isolated tissue or cell line from a patient (e.g., for diagnosis or ex vivo applications), who has a condition contemplated herein or a symptom of a condition contemplated herein, with the purpose to cure, heal, alleviate, relieve, alter, remedy, ameliorate, improve or affect a condition contemplated herein, or the symptoms of a condition contemplated herein. Such treatments may be specifically tailored or modified, based on knowledge obtained from the field of pharmacogenomics.

Compositions

The compositions containing the compound(s) described herein include in one aspect a pharmaceutical composition comprising at least one compound as described herein and at least one pharmaceutically acceptable carrier. In certain embodiments, the composition is formulated for an administration route such as oral or parenteral, for example, transdermal, transmucosal (e.g., sublingual, lingual, (trans) buccal, (trans)urethral, vaginal (e.g., trans- and perivaginally), (intra)nasal and (trans)rectal, intravesical, intrapulmonary, intraduodenal, intragastrical, intrathecal, subcutaneous, intramuscular, intradermal, intra-arterial, intravenous, intrabronchial, inhalation, and topical administration.

Methods of Treating Cancer with Dual AR and ZIP9 Inhibitors

The disclosure includes a method of treating a cancer using compounds that inhibit AR and ZIP9 (also known as SLC39A9). The method includes administering to a subject in need thereof a composition comprising a therapeutically effective amount of at least one active agent that inhibits androgen receptor (AR) and ZIP9.

In certain embodiments, the cancer is not prostate cancer or testicular cancer. In certain embodiments, the cancer is not testicular cancer. In certain embodiments, the cancer is not AR dependent. In certain embodiments, the cancer does not express AR. In certain embodiments, any AR expressed in the cancer does not have significant functional effect on the cancer. By "no significant functional effect" it is meant that any transcriptional activity resulting from presence of AR has no meaningful biological, proliferative, stimulatory, and/or growth effect on the cancer. The lack of a significant functional effect can be a result of, for example, the presence of very low amounts of AR in the cancer tissue. In various embodiments, the method is suitable for treating non-gonadal tissues and for treating cancers that do not occur in gonadal tissues. Examples of gonadal tissues include testicles and ovaries.

In various embodiments, the method is directed to treating cancerous tumors and/or cells that do not have detectable AR levels. I Whether an AR level is detectable is determined using standard immunohistochemistry and quantitation. In various embodiments, the detection of AR is performed using heat-induced epitope retrieval with AR-specific antibody as known in the art and as detailed herein. In various embodiments, the cancer is or contains a plurality of cancerous cells, wherein the cancerous cells do not have detectable levels of AR as measured by immunohistochemistry relative to a known AR expressing and AR responsive tumor such as prostate cancer.

The methods described herein are surprising and unexpected, at least because the dual AR/ZIP9 inhibitors described herein have anticancer activity in tumors that do not express any AR and/or have AR levels that have no significant functional effect on the cancer. Importantly, ZIP9 was not known to be an androgen receptor, nor was it known to be inhibited by AR inhibitors. ZIP9 is also known as SLC39A9.

Non-limiting examples of cancer include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, lung cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. In certain embodiments, the cancer treated is benign or malignant melanoma. In other embodiments, the pancreatic cancer is pancreatic ductal adenocarcinoma (PDAC).

The at least one active agent is, in certain embodiments, bicalutamide, enzalutamide, flutamide, nilutamide, apalutamide (ARN-509), darolutamide (ODM-201), ralaniten (EPI-001), or dimethylcurcumin (ASC-J9).

In various embodiments, the method includes administering an additional therapeutic agent. The additional therapeutic agent can be administered sequentially or concurrently with the at least one active agent. The additional therapeutic agents is, in certain embodiments, an agent that treats cancer. In other embodiments, the additional therapeutic agent is an agent that reduces or alleviates symptoms or side-effects associated with administration of the at least one active agent or of another therapeutic agent.

In various embodiments, the additional therapeutic agent is selected from the group consisting of a chemotherapeutic agent and radiation. Non-limiting suitable chemotherapeutic agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, and mixtures thereof.

In certain embodiments, the subject is male. In one embodiment, the subject is human. The method, in various embodiments, further includes selectively reducing tumor proliferation in a male subject compared to a female subject. The therapeutic effect of administering the AR and/or ZIPS inhibitor is, in certain embodiments greater in a male subject than in a female subject.

In one embodiment, the at least one active agent is administered at a lower dose than the lowest standard dose for the at least one active agent. For example, if the approved dose for an AR inhibitor is 25 mg per day, then the amount of that AR inhibitor administered according to the methods herein is less than 25 mg per day. Both the amount and the frequency of administration can be lower than the standard dose for a particular AR inhibitor.

In one embodiment, the method includes identifying a subject that has failed at least one prior cancer therapy prior to the administering; and administering the at least one active agent to the subject that has failed at least one prior cancer therapy. The phrase "failed at least one prior cancer therapy" as used herein means that the subject had a standard course of treatment with at least one chemotherapeutic agent, radiation, or a combination of thereof, such as one of the chemotherapeutic agents as described herein, and had no clinically significant improvement in their health.

In one embodiment, a method of reducing proliferation of cells in a cancerous tumor is provided. The method includes contacting cells in the cancerous tumor with at least one active agent that inhibits androgen receptor (AR) and ZIP9; and reducing the proliferation of cells in the cancerous tumor, wherein the cancerous tumor is not prostate cancer.

In various embodiments, the cancerous tumor is melanoma. In other embodiments, the cancerous tumor is pancreatic ductal adenocarcinoma (PDAC). In certain embodiments, the at least one active agent is bicalutamide, enzalutamide, flutamide, nilutamide, apalutamide (ARN-509), darolutamide (ODM-201), ralaniten (EPI-001), or dimethylcurcumin (ASC-J9).

In another embodiment, the method further includes exposing cells in the cancerous tumor with an additional therapeutic agent. In various embodiments, the exposing to an additional therapeutic agent is sequential or concurrent with the contacting with the at least one active agent. In various embodiments, therapeutic agent is selected from the group consisting of a chemotherapeutic agent and radiation. In various embodiments, the cells are male mammal cells. In certain embodiments, the mammal is human.

In various embodiments, a method of treating cancer includes administering to a subject in need thereof a composition comprising a therapeutically effective amount of at least one active agent that inhibits ZIP9, and wherein the cancer is not prostate cancer.

In various embodiments, a method of treating cancer includes administering to a subject in need thereof a composition comprising a therapeutically effective amount of at least one active agent that inhibits ZIP9, and wherein the cancer is not testicular cancer.

In various embodiments, a method of treating cancer includes administering to a subject in need thereof a composition comprising a therapeutically effective amount of at least one active agent that inhibits ZIP9, and wherein the cancer is not prostate cancer or testicular cancer.

The methods described herein include administering to the subject a therapeutically effective amount of at least one compound described herein, which is optionally formulated in a pharmaceutical composition. In various embodiments, a therapeutically effective amount of at least one compound described herein present in a pharmaceutical composition is the only therapeutically active compound in a pharmaceutical composition. In certain embodiments, the method further comprises administering to the subject an additional therapeutic agent that treats cancer.

Mortality and Proliferation of Cancers in Males vs. Females

Figure 8:
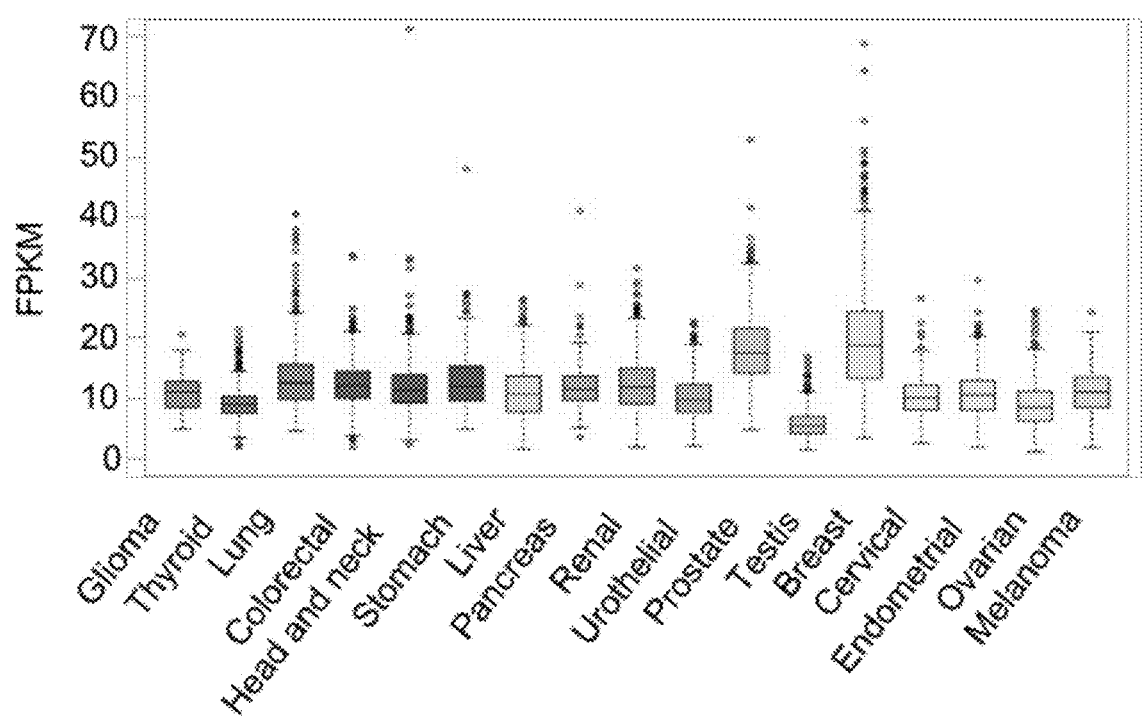
FIG. 8 shows RNA-seq data for ZIP9/SLC39A9 in 17 different human cancer types. (FPM: Fragments Per Kilobase of exon per Million reads) (TCGA). RNA cancer tissue category is calculated based on mRNA expression levels across all 17 cancer tissues. The dataset is visualized with box plots, shown as median and 25th and 75th % tiles. ZIP9 is expressed in all 17 tumor types examined in this study.

For most cancer types, incidence and mortality are higher in males than in females, even after controlling for known epidemiologic risk factors (FIG. 1). Although this sex difference has been appreciated for at least 75 years, the mechanism(s) responsible are only now emerging. It has unexpectedly been discovered that sex steroid signaling through nonclassical receptors is likely a major driver of the disparate cancer outcomes between females and males. Here it is demonstrated that cancer in males is further accelerated by pro-tumorigenic effects of testosterone, and surprisingly, that these effects are independent of the classic androgen receptor (AR). These data from medically relevant preclinical models of melanoma and pancreatic ductal carcinoma (PDAC) provide a strong indication that testosterone signaling through a newly discovered nonclassical G protein-coupled androgen receptor and zinc channel, called ZIP9 (SLC39A9). This membrane receptor is broadly expressed in most tissues (FIG. 8), drives cancer cell proliferation, activates zinc dependent MAPK and YAP cascades, and contributes to sex differences in cancer pathobiology.

As shown herein, testosterone promotes proliferation of normal primary melanocytes and melanoma cells in a saturable manner. This finding was unexpected, as these cells do not express the classic androgen receptor (AR). Data obtained using CRISPR-Cas9 mediated ZIP9 deletion and Reverse Phase Protein Arrays (RPPA), show that the testosterone effects are mediated entirely by ZIP9, require cytoplasmic zinc influx, and are associated with downstream activation of YAP and MAPK. It was also determined that ZIP9 is pharmacologically inhibited by FDA approved agents that were designed to block the classic nuclear AR. ZIP9 has been little studied in cancer, and has not been considered as a possible therapeutic target. Without being bound by theory, it is believed that testosterone promotes tumor cell proliferation by activating ZIP9 and modulating downstream zinc-dependent YAP and MAPK signaling.

In experiments using medically relevant preclinical murine and human melanoma and PDAC models that do not express AR, tumors consistently grew more quickly in males compared to females, and this difference depended on ZIP9. Further, systemic delivery of bicalutamide or apalutamide, synthetic small molecule AR antagonists, inhibited melanoma growth in male mice, but had no effect on the same tumors grown in female mice. These compounds also had no significant effect on tumors with engineered ZIP9 loss, in either male or female mice. Without being bound by theory, normal physiologic testosterone in males activates ZIP9, which promotes tumor growth.

In certain embodiments, administering the compound(s) described herein to the subject allows for administering a lower dose of an additional therapeutic agent as compared to the dose of the additional therapeutic agent alone that is required to achieve similar results in treating a cancer in the subject. For example, in certain embodiments, the compound(s) described herein enhance(s) the activity of the additional therapeutic compound, thereby allowing for a lower dose of the additional therapeutic compound to provide the same effect.

In certain embodiments, the compound(s) described herein and the therapeutic agent are co-administered to the subject. In other embodiments, the compound(s) described herein and the therapeutic agent are coformulated and co-administered to the subject.

In certain embodiments, the subject is a mammal. In other embodiments, the mammal is a human.

Combination Therapies

The compounds useful within the methods described herein can be used in combination with one or more additional therapeutic agents useful for treating cancer. These additional therapeutic agents may comprise compounds that are commercially available or synthetically accessible to those skilled in the art. These additional therapeutic agents are known to treat or reduce the symptoms, of cancer.

In certain embodiments, the compounds described herein can be used in combination with radiation therapy. In other embodiments, the combination of administration of the compounds described herein and application of radiation therapy is more effective in treating or preventing cancer than application of radiation therapy by itself. In yet other embodiments, the combination of administration of the compounds described herein and application of radiation therapy allows for use of lower amount of radiation therapy in treating the subject.

In various embodiments, a synergistic effect is observed when a compound as described herein is administered with one or more additional therapeutic agents or compounds. A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of cancer. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions described herein to a patient, preferably a mammal, more preferably a human, may be carried out using known procedures, at dosages and for periods of time effective to treat cancer in the patient. An effective amount of the therapeutic compound necessary to achieve a therapeutic effect may vary according to factors such as the state of the disease or disorder in the patient; the age, sex, and weight of the patient; and the ability of the therapeutic compound to treat cancer in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound described herein is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds described herein employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the compound(s) described herein are dictated by and directly dependent on (a) the unique characteristics of the therapeutic compound and the particular therapeutic effect to be achieved, and (b) the limitations inherent in the art of compounding/formulating such a therapeutic compound.

In certain embodiments, the compositions described herein are formulated using one or more pharmaceutically acceptable excipients or carriers. In certain embodiments, the pharmaceutical compositions described herein comprise a therapeutically effective amount of a compound described herein and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions described herein are administered to the patient in dosages that range from one to five times per day or more. In other embodiments, the compositions described herein are administered to the patient in range of dosages that include, but are not limited to, once every day, every two, days, every three days to once a week, and once every two weeks. It is readily apparent to one skilled in the art that the frequency of administration of the various combination compositions described herein varies from individual to individual depending on many factors including, but not limited to, age, disease or disorder to be treated, gender, overall health, and other factors. Thus, administration of the compounds and compositions described herein should not be construed to be limited to any particular dosage regime and the precise dosage and composition to be administered to any patient is determined by the attending physician taking all other factors about the patient into account.

The compound(s) described herein for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 350 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In certain embodiments, the dose of a compound described herein is from about 1 mg and about 2,500 mg. In certain embodiments, a dose of a compound described herein used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in certain embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, a composition as described herein is a packaged pharmaceutical composition comprising a container holding a therapeutically effective amount of a compound described herein, alone or in combination with a second pharmaceutical agent; and instructions for using the compound to treat, prevent, or reduce one or more symptoms cancer in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other anticancer agents.

Routes of administration of any of the compositions described herein include oral, nasal, rectal, intravaginal, parenteral, buccal, sublingual or topical. The compounds for use in the compositions described herein can be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions described herein are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compound(s) described herein can be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Compositions as described herein can be prepared, packaged, or sold in a formulation suitable for oral or buccal administration. A tablet that includes a compound as described herein can, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, dispersing agents, surface-active agents, disintegrating agents, binding agents, and lubricating agents.

Suitable dispersing agents include, but are not limited to, potato starch, sodium starch glycollate, poloxamer 407, or poloxamer 188. One or more dispersing agents can each be individually present in the composition in an amount of about 0.01% w/w to about 90% w/w relative to weight of the dosage form. One or more dispersing agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Surface-active agents (surfactants) include cationic, anionic, or non-ionic surfactants, or combinations thereof. Suitable surfactants include, but are not limited to, behentrimonium chloride, benzalkonium chloride, benzethonium chloride, benzododecinium bromide, carbethopendecinium bromide, cetalkonium chloride, cetrimonium bromide, cetrimonium chloride, cetylpyridine chloride, didecyldimethylammonium chloride, dimethyldioctadecylammonium bromide, dimethyldioctadecylammonium chloride, domiphen bromide, lauryl methyl gluceth-10 hydroxypropyl dimonium chloride, tetramethylammonium hydroxide, thonzonium bromide, stearalkonium chloride, octenidine dihydrochloride, olaflur, N-oleyl-1,3-propanediamine, 2-acrylamido-2-methylpropane sulfonic acid, alkylbenzene sulfonates, ammonium lauryl sulfate, ammonium perfluorononanoate, docusate, disodium cocoamphodiacetate, magnesium laureth sulfate, perfluorobutanesulfonic acid, perfluorononanoic acid, perfluorooctanesulfonic acid, perfluorooctanoic acid, potassium lauryl sulfate, sodium alkyl sulfate, sodium dodecyl sulfate, sodium laurate, sodium laureth sulfate, sodium lauroyl sarcosinate, sodium myreth sulfate, sodium nonanoyloxybenzenesulfonate, sodium pareth sulfate, sodium stearate, sodium sulfosuccinate esters, cetomacrogol 1000, cetostearyl alcohol, cetyl alcohol, cocamide diethanolamine, cocamide monoethanolamine, decyl glucoside, decyl polyglucose, glycerol monostearate, octylphenoxypolyethoxyethanol CA-630, isoceteth-20, lauryl glucoside, octylphenoxypolyethoxyethanol P-40, Nonoxynol-9, Nonoxynols, nonyl phenoxypolyethoxylethanol (NP-40), octaethylene glycol monododecyl ether, N-octyl beta-D-thioglucopyranoside, octyl glucoside, oleyl alcohol, PEG-10 sunflower glycerides, pentaethylene glycol monododecyl ether, polidocanol, poloxamer, poloxamer 407, polyethoxylated tallow amine, polyglycerol polyricinoleate, polysorbate, polysorbate 20, polysorbate 80, sorbitan, sorbitan monolaurate, sorbitan monostearate, sorbitan tristearate, stearyl alcohol, surfactin, Triton X-100, and Tween 80. One or more surfactants can each be individually present in the composition in an amount of about 0.01% w/w to about 90% w/w relative to weight of the dosage form. One or more surfactants can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable diluents include, but are not limited to, calcium carbonate, magnesium carbonate, magnesium oxide, sodium carbonate, lactose, microcrystalline cellulose, calcium phosphate, calcium hydrogen phosphate, and sodium phosphate, Cellactose® 80 (75% α-lactose monohydrate and 25% cellulose powder), mannitol, pre-gelatinized starch, starch, sucrose, sodium chloride, talc, anhydrous lactose, and granulated lactose. One or more diluents can each be individually present in the composition in an amount of about 0.01% w/w to about 90% w/w relative to weight of the dosage form. One or more diluents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable granulating and disintegrating agents include, but are not limited to, sucrose, copovidone, corn starch, microcrystalline cellulose, methyl cellulose, sodium starch glycollate, pregelatinized starch, povidone, sodium carboxy methyl cellulose, sodium alginate, citric acid, croscarmellose sodium, cellulose, carboxymethylcellulose calcium, colloidal silicone dioxide, crosspovidone and alginic acid. One or more granulating or disintegrating agents can each be individually present in the composition in an amount of about 0.01% w/w to about 90% w/w relative to weight of the dosage form. One or more granulating or disintegrating agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable binding agents include, but are not limited to, gelatin, acacia, pre-gelatinized maize starch, polyvinylpyrrolidone, anhydrous lactose, lactose monohydrate, hydroxypropyl methylcellulose, methylcellulose, povidone, polyacrylamides, sucrose, dextrose, maltose, gelatin, polyethylene glycol. One or more binding agents can each be individually present in the composition in an amount of about 0.01% w/w to about 90% w/w relative to weight of the dosage form. One or more binding agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Suitable lubricating agents include, but are not limited to, magnesium stearate, calcium stearate, hydrogenated castor oil, glyceryl monostearate, glyceryl behenate, mineral oil, polyethylene glycol, poloxamer 407, poloxamer 188, sodium laureth sulfate, sodium benzoate, stearic acid, sodium stearyl fumarate, silica, and talc. One or more lubricating agents can each be individually present in the composition in an amount of about 0.01% w/w to about 90% w/w relative to weight of the dosage form. One or more lubricating agents can each be individually present in the composition in an amount of at least, greater than, or less than about 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90% w/w relative to weight of the dosage form.

Tablets can be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Tablets can also be enterically coated such that the coating begins to dissolve at a certain pH, such as at about pH 5.0 to about pH 7.5, thereby releasing a compound as described herein. The coating can contain, for example, EUDRAGIT® L, S, FS, and/or E polymers with acidic or alkaline groups to allow release of a compound as described herein in a particular location, including in any desired section(s) of the intestine. The coating can also contain, for example, EUDRAGIT® RL and/or RS polymers with cationic or neutral groups to allow for time controlled release of a compound as described herein by pH-independent swelling.

Parenteral Administration

For parenteral administration, the compounds as described herein may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as Ph. Helv or similar alcohol.

Additional Administration Forms

Additional dosage forms suitable for use with the compound(s) and compositions described herein include dosage forms as described in U.S. Pat. Nos. 6,340,475; 6,488,962; 6,451,808; 5,972,389; 5,582,837; and 5,007,790. Additional dosage forms suitable for use with the compound(s) and compositions described herein also include dosage forms as described in U.S. Patent Applications Nos. 20030147952; 20030104062; 20030104053; 20030044466; 20030039688; and 20020051820. Additional dosage forms suitable for use with the compound(s) and compositions described herein also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations described herein can be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use with the method(s) described herein may be administered in the form of microparticles, for example, by injection or in the form of wafers or discs by implantation.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions described herein. Thus, single unit dosage forms suitable for oral administration, such as tablets, capsules, gelcaps, and caplets, that are adapted for controlled-release are encompassed by the compositions and dosage forms described herein.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" is defined herein as a compound or compounds, including, but not limited to, polymers, polymer matrices, gels, permeable membranes, liposomes, or microspheres or a combination thereof that facilitates the controlled-release of the active ingredient. In one embodiment, the compound(s) described herein are administered to a patient, alone or in combination with another pharmaceutical agent, using a sustained release formulation. In one embodiment, the compound(s) described herein are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound described herein depends on the age, sex and weight of the patient, the current medical condition of the patient and the progression of cancer in the patient being treated. The skilled artisan is able to determine appropriate dosages depending on these and other factors.

A suitable dose of a compound described herein can be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the compound(s) described herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced to a level at which the improved disease is retained. In certain embodiments, patients require intermittent treatment on a long-term basis upon any recurrence of symptoms and/or infection.

The compounds described herein can be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

EXAMPLES

Various embodiments of the present application can be better understood by reference to the following Examples which are offered by way of illustration. The scope of the present application is not limited to the Examples given herein.

Contribution of Nonclassical Androgen Signaling to Sex Differences in Cancer

Sex differences in cancer incidence and mortality were reported at least as early as 1949. Consistent with those findings, continually accumulating data from the U.S. and worldwide clearly demonstrate that both cancer incidence and mortality are higher in males than in females (SEER-.cancer.gov, International Agency for Research on Cancer, World Health Organization GLOBOCAN2018). In the U.S., males are 15% more likely to develop cancer than females, and 40% are more likely to die of this disease. These sex differences are observed in the majority of cancer types from non-reproductive tissues (FIG. 1), and remain even after controlling for known risk factors such as environmental and occupational exposures. Here it is shows that testosterone, which circulates at higher levels in males vs. females, promotes cancer growth of cancer cells and tumors that do not express the classic androgen receptor, and that, this testosterone activity depends on a newly recognized non-classical testosterone receptor called ZIP9.

Testosterone Promotes Cancer by Activating ZIP9 and Downstream Zinc Dependent YAP and MAPK Signaling.

Testosterone is the most abundant androgen in males and circulates at much higher levels in males (630 ng/dl) than in females (32 ng/dl). Here it is shown that testosterone promotes proliferation of mouse and human melanoma cells, which do not express AR. Without being bound by theory, it is believed that differences in endogenous testosterone result in differential activation of ZIP9, which thereby contributes to the male vs. female sex differences in human cancer incidence and survival.

Figure 2A:
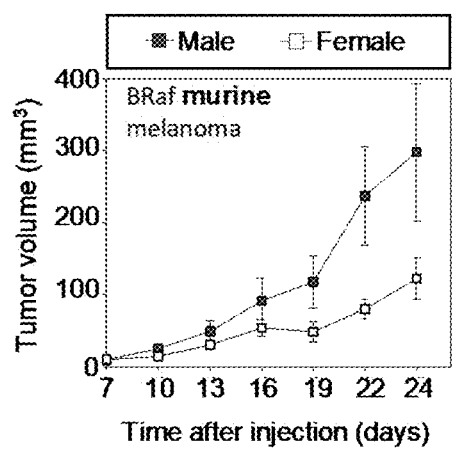
FIGS. 2A-2B show how biologic sex influences melanoma progression and prognosis.
Figure 2B:
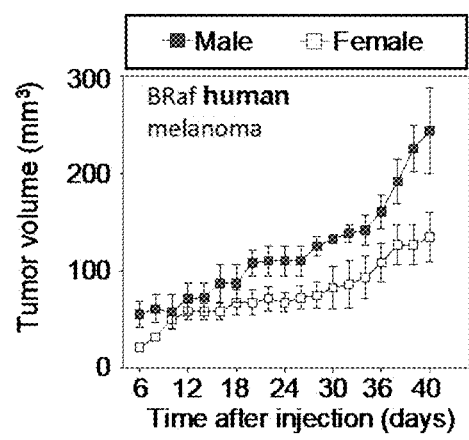

Here it is shown that medically-relevant modern preclinical melanoma models recapitulate the female:male survival disparity observed in people. In syngeneic murine melanoma, YUMM1.7 ($BRaf^{V600E/wt}$; $Pten^{-/-}CdkN2a^{-/-}$) tumors consistently grew faster in sexually mature C57BL/6 males compared to matched females (FIG. 2; left panel). Increased growth of human WM46 melanoma ($BRaf^{V600E}$; $CDK4^{R24C}$) in male vs. female immunodeficient SCID mice was observed, suggesting that the growth difference does not depend on functional T or B cell mediated immune responses (FIG. 2; right panel). Pure populations of normal melanocytes and melanoma cells were exposed to physiologically relevant concentrations of testosterone (T) to test whether testosterone promotion of tumor growth may result, at least in part, from tumor cell intrinsic effects. (FIG. 3A). It was also tested whether dihydrotestosterone (DHT) affected proliferation, as DHT binds AR with 4× the affinity of T, dissociates from AR 3× slower than T, and is therefore classically considered the more biologically active androgen. In primary melanocytes, as well as mouse and human melanoma cells, T, but not DHT, markedly increased cellular proliferation (FIG. 3A). The proliferative response to T correlated with its concentration and was saturable, strongly suggesting a specific receptor-mediated process (FIG. 3B). However, none of these testosterone sensitive cells express the classic androgen receptor AR (FIG. 3C).

Recent studies in fish identified a surface androgen receptor, called ZIP9, that is completely distinct from nAR. The human ZIP9 homolog is broadly expressed in most tissues (FIG. 8), and it was determined that it is expressed in both normal melanocytes and all melanoma lines tested to date (FIG. 3C). Consistent with the idea that ZIP9 may mediate the testosterone activity in these cells, competitive binding assays have demonstrated that ZIP9 is highly specific for testosterone, with relatively low affinity for DHT and androstenedione, which, without being bound by theory, explains why DHT did not promote proliferation (FIG. 3A).

Figures 4A, 4B, 4C, 4D:
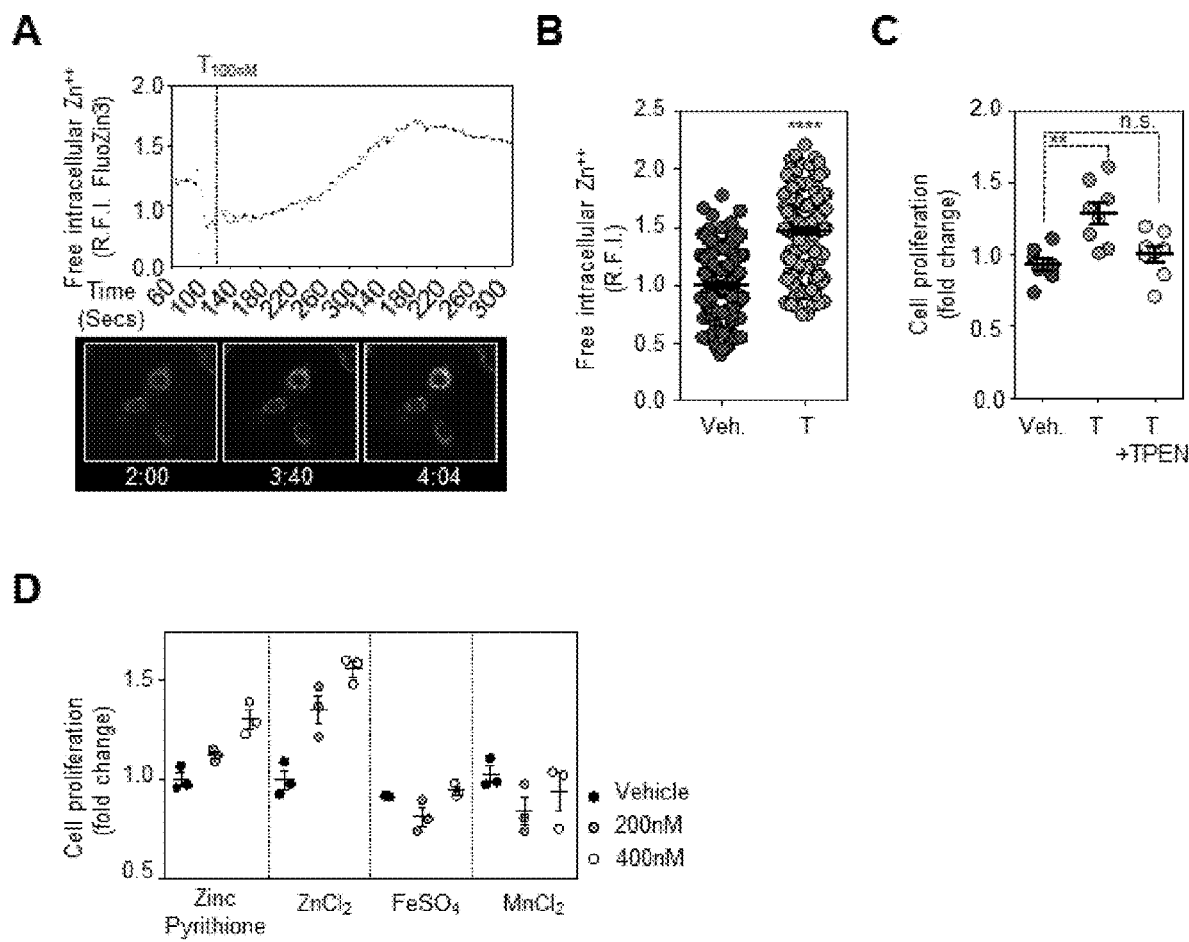
FIGS. 4A-4D show that testosterone triggered cytosolic $Zn^{++}$ influx is necessary for testosterone induced hyperproliferation in human melanoma cells (WM46).

ZIP9 is a member of the ZIP family (Zrt-Irt-like proteins) that function to transport zinc into the cystosol from the extracellular space or from intracellular compartments. ZIP9 is also thought function as a G coupled GPCR. Zinc is essential for cell differentiation, viability, and proliferation. It was next questioned whether testosterone triggered zinc influx into melanoma cells, and if so, whether that zinc influx was required for the increased proliferation. In an in vitro experiment using the zinc sensitive fluorescent dye Fluo-Zin 3 in human WM46 melanoma cells, it was observed that testosterone induced a rapid zinc influx over 5 minutes (FIG. 4A). This was followed by a sustained elevation in free cytosolic zinc for at least 2 days in the presence of the androgen (FIG. 4B).

The specific zinc chelator N,N,N',N'-tetrakis (2-pyridinylmethyl)-1,2-ethanediamine (TPEN), completely blocked the testosterone induced proliferation (FIG. 4C), while having no significant effect on its own. Thus, without being bound by theory, this finding suggests that cytosolic zinc influx is necessary for testosterone-induced melanoma cell proliferation.

Figures 5A, 5B, 5C:
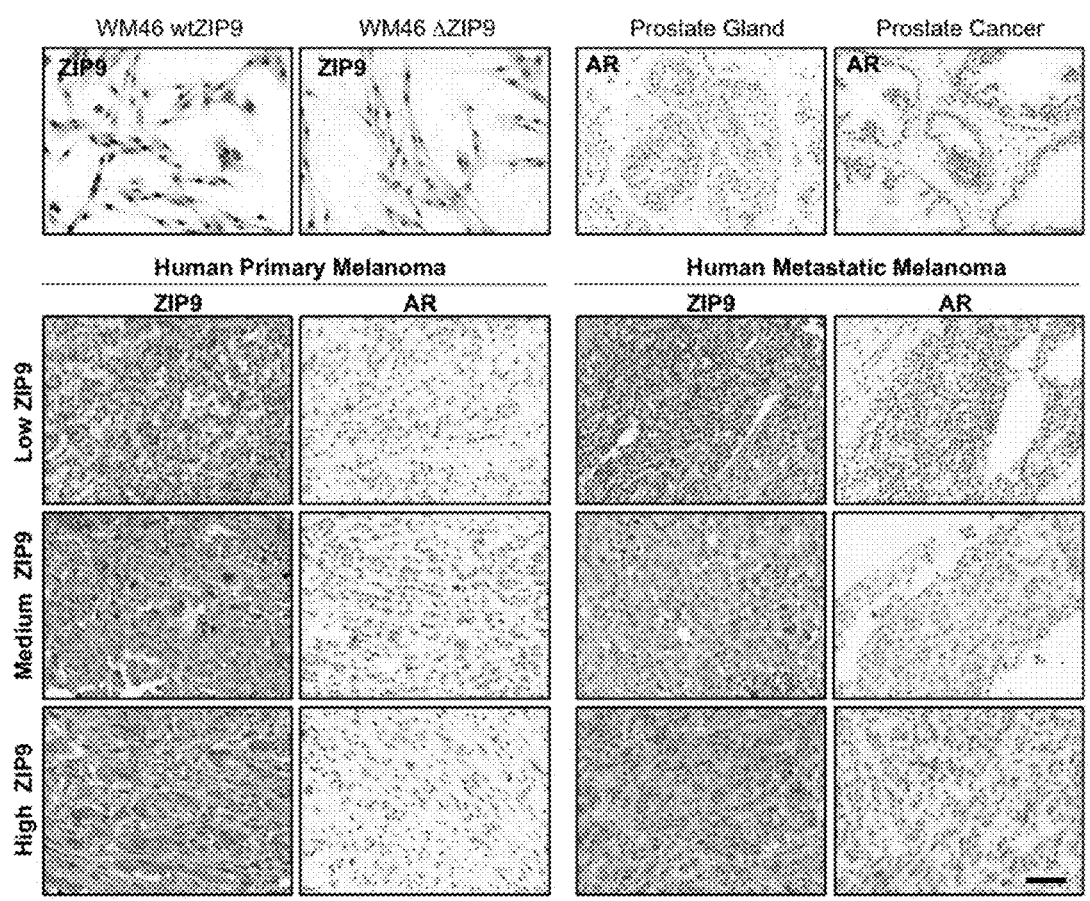
FIGS. 5A-5C show that ZIP9 is broadly expressed in human melanocytic tumors.
Figure 6:
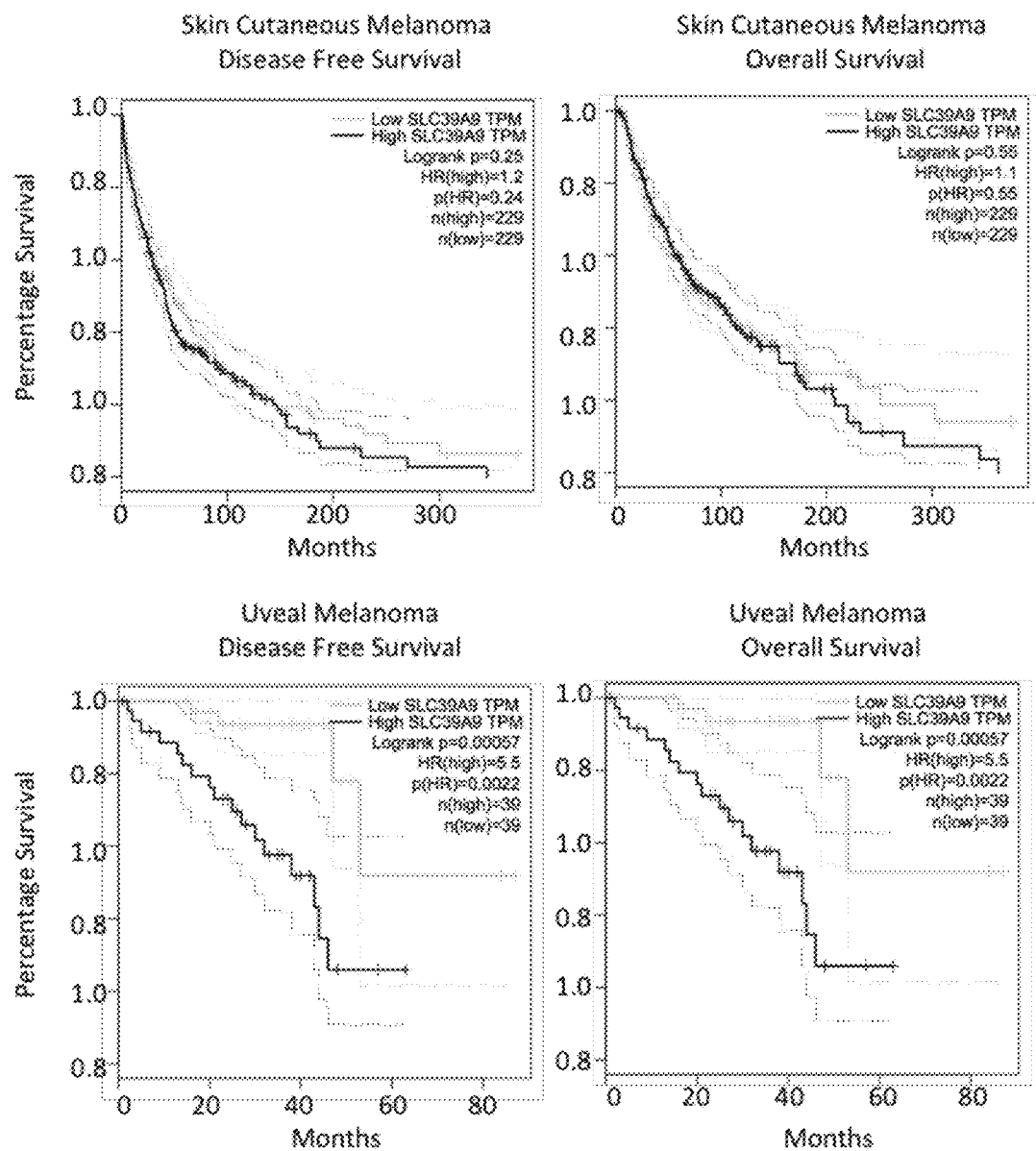
FIG. 6 shows that that high levels of ZIP9/SLC39A9 are associated with bad prognosis in skin cutaneous melanoma and uveal melanoma RNA sequencing expression data of 9,736 tumors and 8,587 normal samples from the TCGA and the GTEx projects, using a standard processing pipeline. Data obtained from GEPIA (Gene Expression Profiling Interactive Analysis).

Next, immunocytochemistry was used to test whether AR and/or ZIP9 protein are expressed in human melanocytic lesions (14 benign nevi, 63 primary melanomas, and 21 metastatic melanomas). AR was determined in tissue sections using the highly controlled CLIA (Clinical Laboratory Improvement Amendments) certified method in the clinical pathology lab at the Hospital of the University of Pennsylvania While AR was readily detectable in prostate tissue used as positive control, AR was not detected in any of the nevi, nor in the melanomas (FIG. 5A). In parallel, the same samples were analyzed for ZIP9. CLIA grade ZIP9 IHC is not available. ZIP9 antibody was validated using parental WM46 ZIP9 positive (wtZIP9) and isogenic ZIP9 negative (ΔZIP9) isogenic cell lines. ZIP9 protein was observed in 100% of the nevi, 97% of primary melanomas and 100% of the metastatic samples (FIG. 5B). Further, ZIP9 relative staining intensity positively correlated with tumor stage (FIG. 5C). In line with this results, Importantly, high levels of ZIP9 expression are associated with poor prognosis in skin cutaneous melanoma and uveal melanoma (FIG. 6).

Figure 7A:
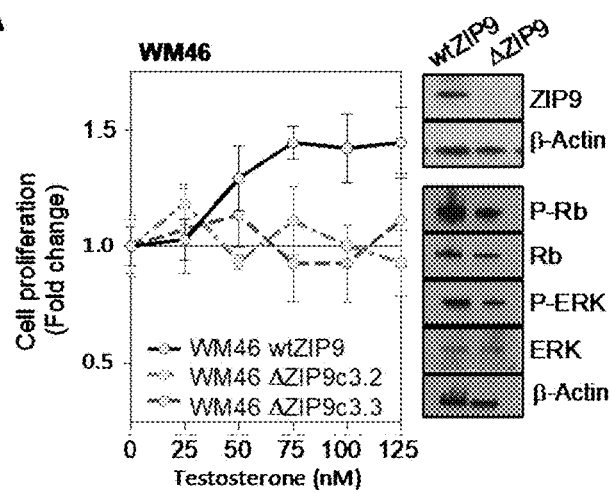
FIGS. 7A-7D show that WM46 and YUMM1.7 melanoma cells engineered to lack Zip9 (ΔZIP9) do not respond to testosterone.
Figure 7B:
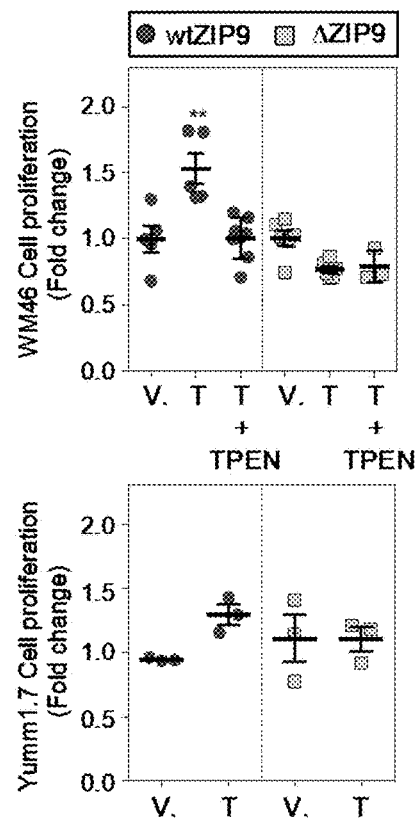

To determine whether ZIP9 is the receptor that mediates testosterone effects in melanoma cells, clonal populations of human cancer cells (derived from melanoma and PDAC) with targeted CRISPR-Cas9 mediated ablation of Slc39A9 (gene encoding ZIP9) were established. These cells were designated ΔZIP9 (FIG. 7A). These ΔZIP9 cells are morphologically normal and proliferate, albeit at rates slightly slower than controls. This decreased proliferation is associated with decreased MAPK activity (p-ERK). Human and mouse cells lacking ZIP9 (ΔZIP9) do not respond to testosterone whereas isogenic clones with ZIP9 proliferate faster when treated with testosterone (FIG. 7B).

Figure 7C:
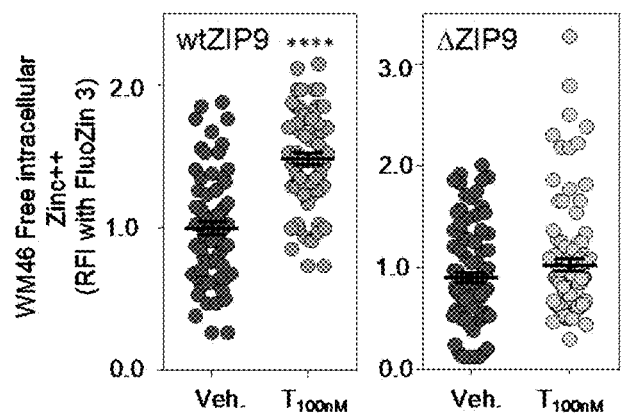
Figure 7D:
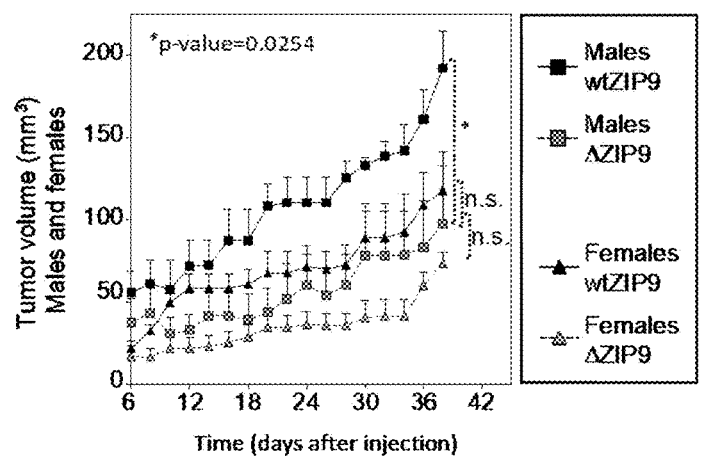

Without being bound by theory, and consistent with the hypothesis that internalization of free zinc in melanoma cells is at least partially ZIP9-dependent, increases in cytosolic zinc were nearly absent in ΔZIP9 cells following exposure to exogenous zinc salt (FIG. 7C), or to testosterone (FIG. 7D). In male host mice, melanomas lacking ZIP9 grew more slowly than matched isogenic tumors that express ZIP9. In female mice, there was no significant difference in tumor growth rate between ZIP9 expressing, and ZIP9 depleted tumors (FIG. 7E).

Figures 9A, 9B, 9C, 9D, 9E:
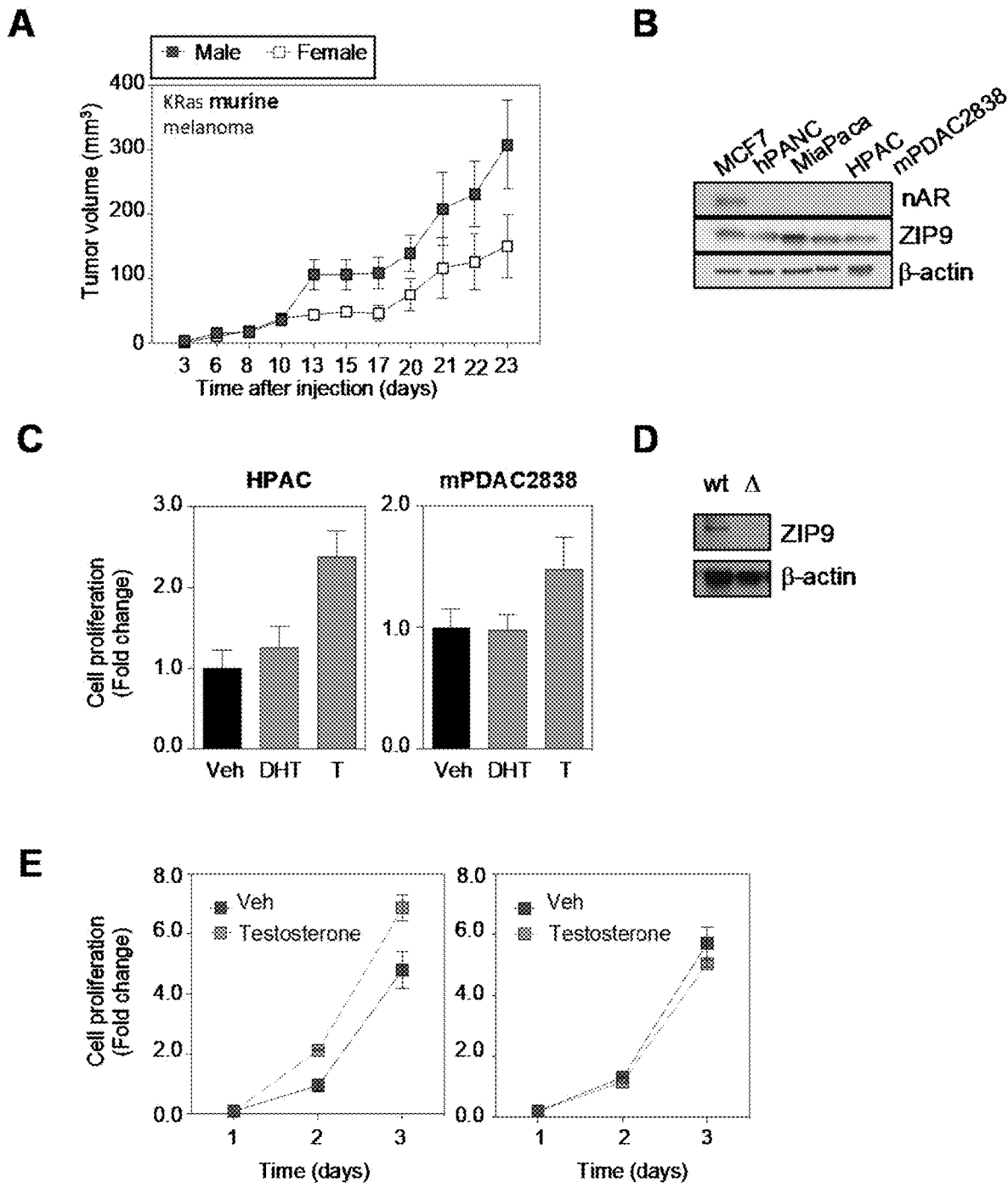
FIGS. 9A-9E show that testosterone promotes proliferation of pancreatic ductal carcinoma (PDAC).

ZIP9 is widely expressed in human cancer (FIG. 8), suggesting that ZIP9 may be a useful target for many cancer types. To test this ZIP9 studies were extended to pancreatic ductal adenocarcinoma (PDAC), another common cancer in people with a large male vs. female sex disparity in incidence and outcome. In a PDAC mouse model, syngeneic murine PDAC tumors progress faster in male vs. female mice (FIG. 9A). Consistent with the hypothesis that non-classical androgen signaling also contributes to the sex gap in PDAC, human and murine PDAC both express ZIP9 and completely lack AR (FIG. 9B). Further, testosterone, but not DHT, promoted PDAC cell proliferation (FIG. 9C). CRISPR-Cas9 was used to generate PDAC cell clones with ZIP9/SLC39A9 ablation (FIG. 9D).

The human cancer sex gap, coupled with the functional ZIP9 experiments described herein, suggest that ZIP9 can be a therapeutic target for melanoma, PDAC, and possibly many other cancers. Although specific ZIP9 inhibitors are not yet developed, here it was shown that the well-known FDA approved non-steroidal AR inhibitor bicalutamide (Casodex) inhibits testosterone effects on cancer cells that lack AR, but that do express ZIP9. Bicalutamide was developed as a prostate cancer therapeutic with higher affinity for the nAR than the earlier compound flutamide or its active metabolite hydroxyflutamide. In clinical practice, bicalutamide and flutamide have now been largely replaced by enzalutamide and apalutamide, which have even higher affinity for nAR, and greater clinical efficacy against prostate cancer.

Figure 10A:
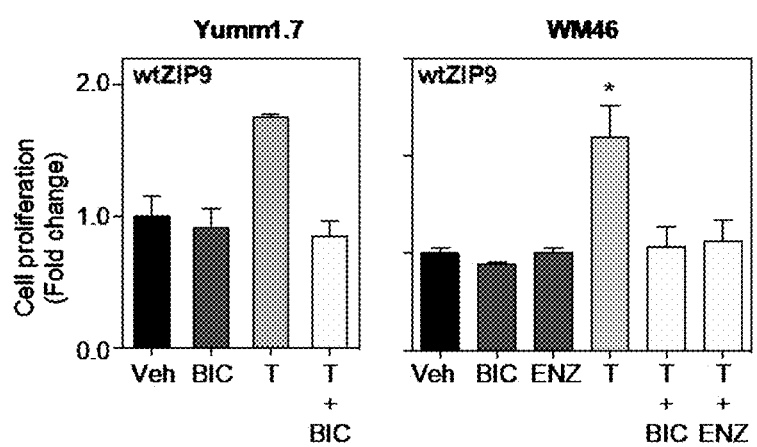
FIGS. 10A-10E show that bicalutamide (BIC) and enzalutamide (ENZ) each block testosterone-induced hyperproliferation in melanoma cells.
Figure 10B:
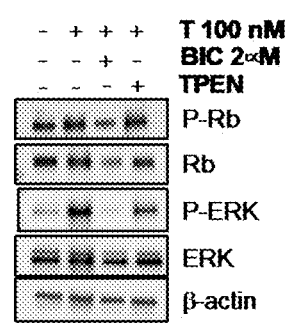
Figure 10C:
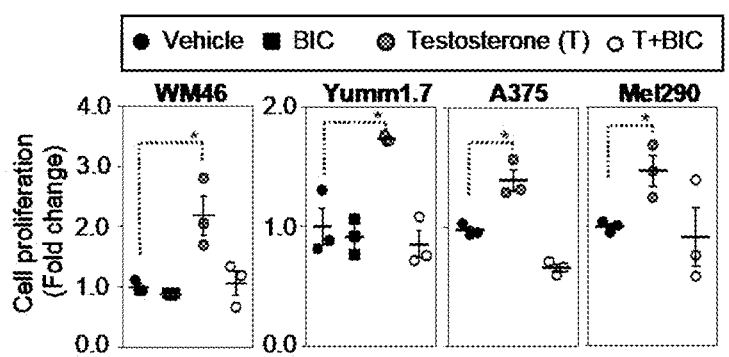
Figure 10D:
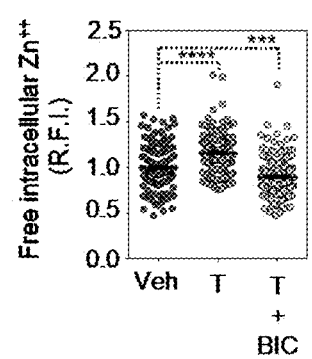
Figure 10E:
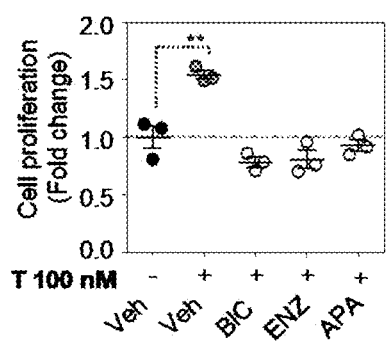
Figure 11:
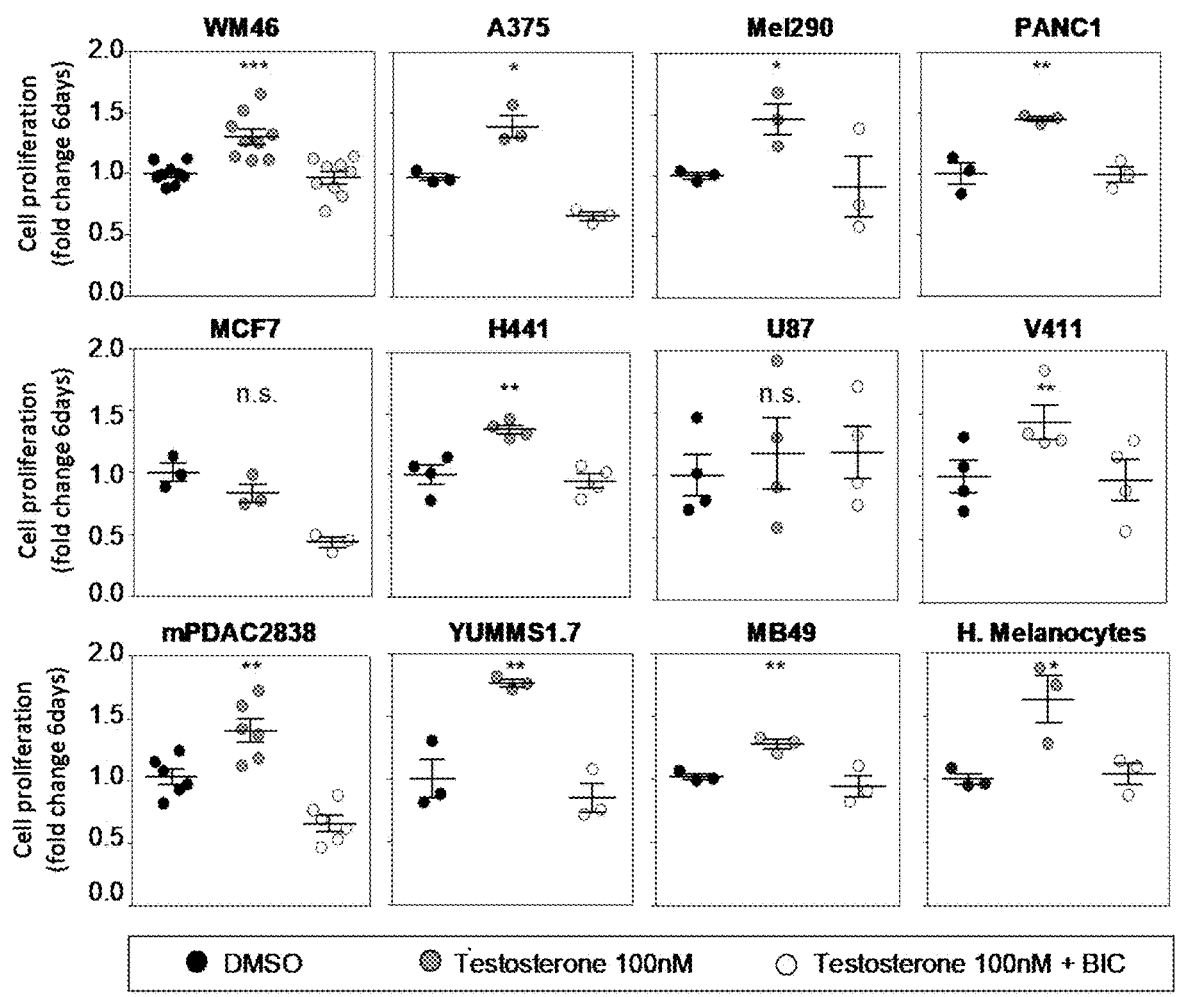
FIG. 11 shows that Bicalutamide (BIC) blocks testosterone-induced hyperproliferation in a majority (10/12) of cell lines derived from diverse human and murine tumor types. **p value<0.0001; p value<0.005; *p value<0.01. (MCF7 and U87 cells did not respond to testosterone.)

In one embodiment, melanoma cells with testosterone+/− were treated with bicalutamide or enzalutamide. While bicalutamide or enzalutamide alone had no effect on cell proliferation, they each completely inhibited the testosterone effect in cells that express ZIP9 (FIG. 10A). Testosterone-driven increase in MAPK activation (p-ERK) was inhibited by either bicalutamide, or the zinc chelator TPEN (FIG. 10B). Cell proliferation driven by testosterone was inhibited by bicalutamide (BIC) in four different cell lines derived from melanoma (both murine and human) (FIG. 10C). Importantly, when combined with bicalutamide, testosterone did not induce zinc influx in WM46 cells (FIG. 10D). In clinical practice, bicalutamide and flutamide have now been largely replaced by enzalutamide and apalutamide, which have even higher affinity for nAR, and greater clinical efficacy against advanced prostate cancer. When treated with 204 Apalutamide, testosterone dependent-increased proliferation was reverted in WM46 (FIG. 10E). In line with the fact that ZIP9 is broadly expressed in humans, a battery of cell lines derived from different tumors responded testosterone, and this effect was inhibited by bicalutamide (FIG. 11).

Without being bound by theory, the effects of bicalutamide/enzalutamide are believed to be completely mediated through ZIP9. But, together with this, ZIP9 is widely expressed in human cancer (FIG. 8), suggesting that ZIP9 may be a useful target for many cancer types.

Testosterone-Driven Increases in Cancer Cell Proliferation Depend on Activation of MAPK and YAP Signaling Downstream of ZIP9 and Zinc Influx.

Testosterone induces a rapid, ZIP9 dependent, increase in free cytosolic zinc that is required for the hyperproliferation. Zinc is required for myriad cellular enzymes and associated biologic process making it difficult to hypothesize a priori, what signaling mechanism(s) downstream of ZIP9 mediate the testosterone induced hyperproliferation. A 450 element Reverse Phase Protein Array analysis of human melanoma cells treated with testosterone for 0, 30 minutes, 60 minutes and 8 hours (FIG. 12A) was performed. While the relative expression of most of the proteins represented on the array was unaffected by testosterone, some proteins were significantly over or underexpressed, including several with tumor promoting or tumor suppressive functions. The downregulated proteins included 14-3-3ε, a tumor suppressor and negative YAP regulator previously implicated in liver, lung, and gastric cancers, and CDKN2A (p16), a cyclin-dependent kinase (CDK) inhibitor, and one of the most studied tumor suppressors.

Figures 12A, 12B:
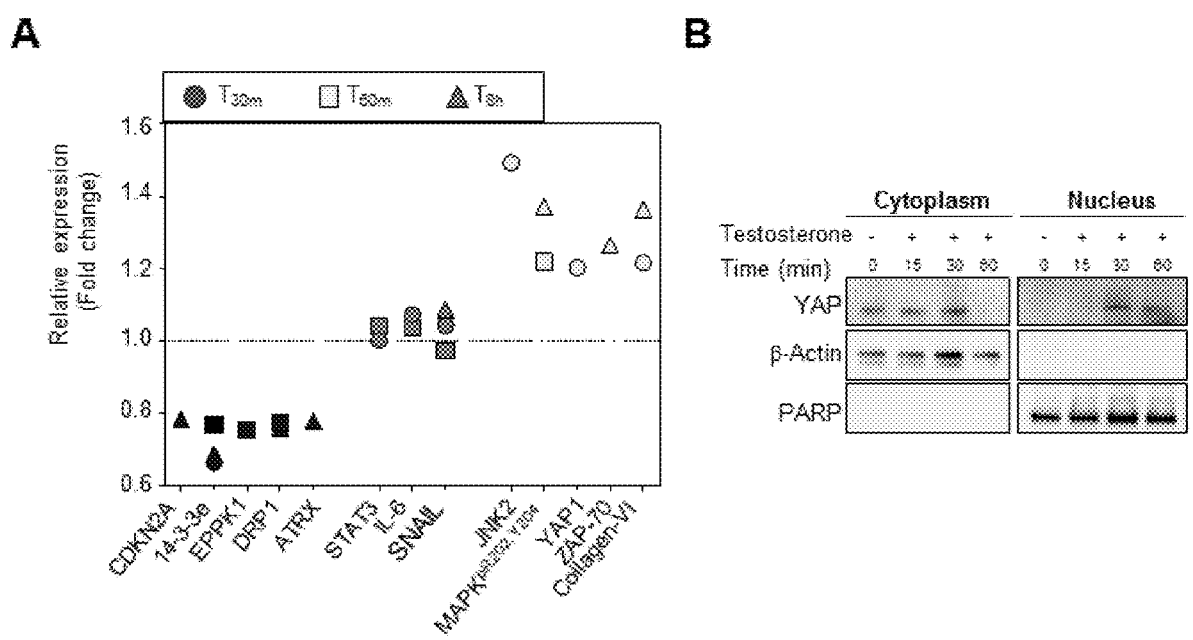
FIGS. 12A-12B shows a Reverse Phase Protein Array (RPPA) analysis of protein expression changes in WM46 human melanoma cells following exposure to testosterone. (For clarity, this figure highlights only a subset of proteins from the entire data set of 450 proteins at 4 time points).

Upregulated proteins included key elements of tumor promoting pathways, most notably phosphorylated ERK (T202; Y204) and YAP1. YAP has not previously been functionally linked to ZIP9, nor to bicalutamide nor to apalutamide. Both p-ERK and YAP are both altered by testosterone (FIGS. 3B and 12B). MAPK/ERK signaling is essential for melanoma, most of which are driven by activating Raf or Ras mutations. This p-ERK induction is likely a specific receptor (ZIP9) mediated process, as it was completely blocked by bicalutamide (BIC), as well as the zinc chelator TPEN (FIG. 10B).

YAP controls diverse cellular processes including proliferation, survival and differentiation, is upregulated in many solid tumors, and is implicated in chemotherapy resistance. It was intriguing to observe YAP1 as one of the top hits on the RPPA because YAP is positively regulated by Goa coupled GPCRs, and early studies indicated that ZIP9, in addition to functioning as a zinc channel, is also a Gi-coupled GPCR. When activated, YAP and the related transcription factor TAZ are dephosphorylated and move from the cytosol to the nucleus. YAP was observed to move from cytoplasm to nucleus within 30-60 minutes of testosterone exposure (FIG. 12B). YAP is a substrate for 14-3-3ε, which sequesters YAP in the cytosol. As 14-3-3ε, was one of the proteins most depleted by testosterone, it is believed, without being bound by theory, that 14-3-3ε loss promotes YAP translocation to the nucleus where it then induces expression of tumor-promoting genes. It is likely that the MAK/ERK changes also contribute to testosterone induced YAP activation, as MEK and ERK1/2 are also major positive YAP regulators.

Pro-Proliferative Effect of Testosterone Through ZIP9 is Inhibited by Drugs that were Originally Designed to Target the Classical Androgen Receptor (AR)

Nonsteroidal anti-androgens in the bicalutamide class that were designed to target AR, can, in certain embodiments, also inhibit ZIP9. Bicalutamide and enzalutamide completely blocked testosterone proliferative effects in human and mouse melanoma cells (FIGS. 10A and 10C). Because these drugs did not affect baseline cellular proliferation rate when used alone, and the cells lack AR, the drugs are believed to prevent the testosterone effects by competing with testosterone for binding to ZIP9. The AR/ZIP9 inhibitors do not affect proliferation rate of ΔZIP9 cells, with or without testosterone.

Figures 13A, 13B, 13C:
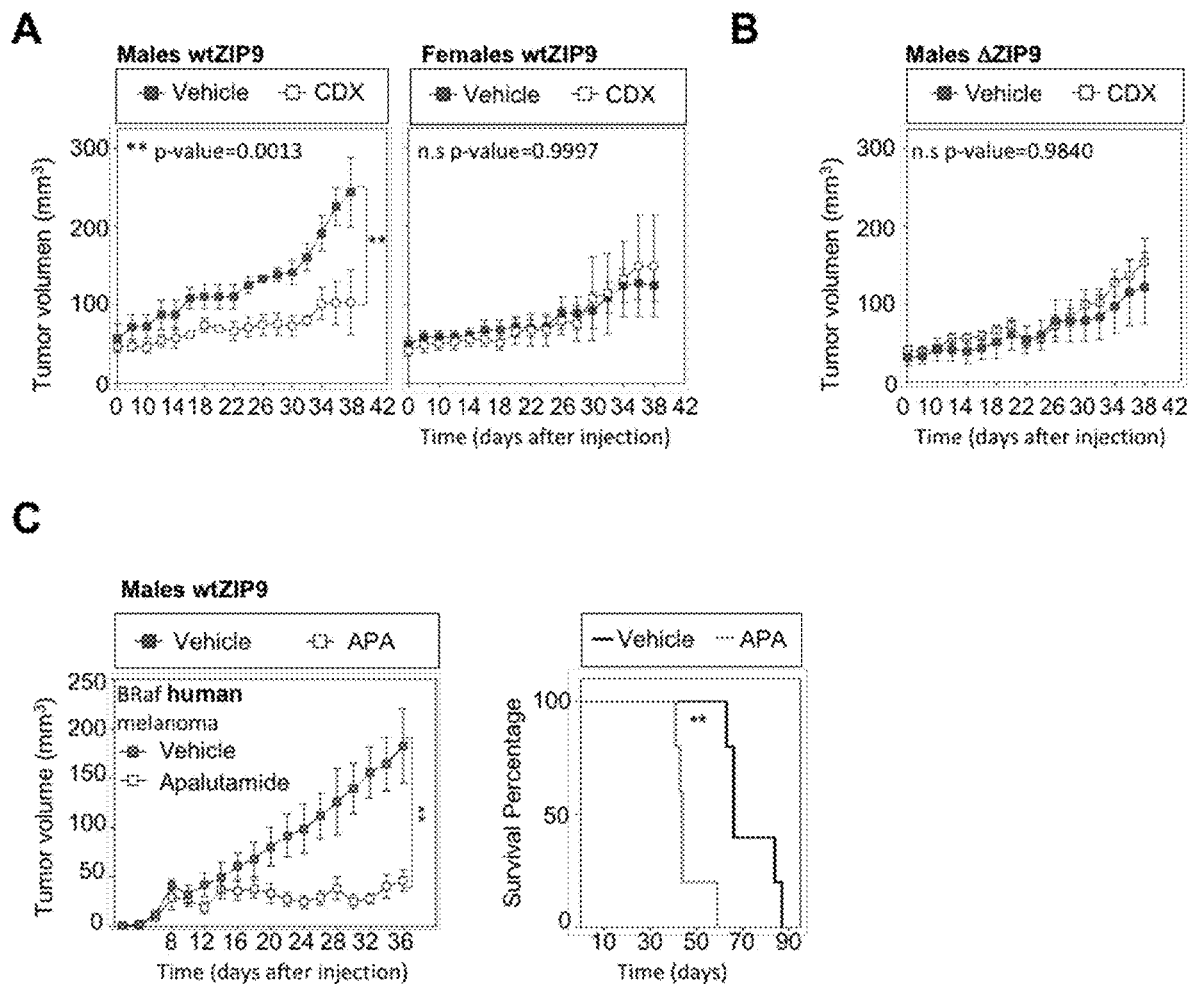
FIGS. 13A-13C show that systemic delivery of bicalutamide (BIC) or apalutamide (APA) inhibits growth of human WM46 melanoma in immunodeficient SCID mice.

Pharmacologic Targeting of Nonclassical Sex Steroid Receptors Inhibits Tumor Growth In Vivo and Extends Survival The tumor-promoting effects of testosterone on early prostate cancer are known, and inhibition of testosterone signaling is a first-line treatment. However, the idea that testosterone regulates growth of other tumor types, especially those such as melanoma and PDAC that do not express AR, is counterintuitive and unexpected. Here it is shown that targeting nonclassical testosterone signaling through ZIP9 is therapeutically useful for cancer (FIG. 13). WM46 human melanoma tumors (which do not express AR) grew faster in male vs. female mice. Systemic delivery of the AR inhibitor bicalutamide (30 mg/kg/day via oral gavage) significantly slowed tumor growth in male mice but had no effect on tumor growth in female mice, strongly suggesting that the anti-tumor activity results from inhibition of endogenous androgen signaling (FIG. 13A). Bicalutamide delays tumor growth by inhibiting ZIP9 as tumors lacking the receptor do not responded to bicalutamide (FIG. 13B). Other AR antagonists such as apalutamide are also active in vivo on ZIPS expressing, AR negative tumors (FIG. 13C).

The terms and expressions employed herein are used as terms of description and not of limitation, and there is no intention in the use of such terms and expressions of excluding any equivalents of the features shown and described or portions thereof, but it is recognized that various modifications are possible within the scope of the embodiments of the present application. Thus, it should be understood that although the present application describes specific embodiments and optional features, modification and variation of the compositions, methods, and concepts herein disclosed may be resorted to by those of ordinary skill in the art, and that such modifications and variations are considered to be within the scope of embodiments of the present application.

Immunohistochemistry and Quantification

FFPE (formalin-fixed paraffin-embedded) tissue microarrays (ME1004h: Malignant melanoma, metastatic malignant melanoma and nevus tissue array) were obtained from US Biomax, Inc. (Derwood, MD). For the staining with anti-ZIPS antibody [(SLC39A9 Antibody (PAS-52485), Thermofisher Scientific, Waltham, MA)], slides were deparaffinized and rehydrated following the standard immunohistochemistry protocol [(xylenes 5 minutes×3, 100% alcohol (5 min.×3), 95% alcohol (5 min.), 80% alcohol (5 min.), 70% alcohol (5 min.), and 50% alcohol (5 min.) and finished with distilled water)]. The antigen retrieval was done by loading the slides into a retriever (Electron Microscopy Sciences EMS) with R-Buffer A. After 20 minutes, samples were allowed to cool for 30 minutes inside the retriever and for 20 minutes at room temperature. Samples were washed twice with PBS and blocked with Dako Dual Endogenous Enzyme Block (Code 52003. Agilent Santa Clara, CA) for 20 minutes at R.T. Samples were washed twice with PBS and blocked for 20 minutes with 2 drops of Vector Avidin Block. After washing twice with PBS, slides were blocked for 20 minutes with two drops of Vector Biotin Block (Avidin/Biotin Blocking kit. SP-2001. Vector Laboratories, Inc. Burlingame, CA). Samples were washed twice with PBS with Protein Block Serum-Free Ready-To-Use for 30 minutes at R.T. (Code X0909. Agilent Santa Clara, CA). Primary antibody was prepared 1:500 in PBST (100 µl per slide) and samples were incubated overnight at 4° C. Samples were washed three times with PBS and incubated with Biotinylated Secondary antibody (Vectastain Kit, Peroxidase Rabbit IgG, PK-4001) for one hour at R.T. After three washes with PBS, ABC reagent (prepared 30 minutes in advance) was added and samples were incubated for 30 minutes at R.T. Samples were washed twice with PBS and incubated for 3 minutes with ImmPACT® DAB Substrate, Peroxidase (HRP) (SK-4105. Vector laboratories, Burlingame, CA). Tissues were counterstained with hematoxylin (30 seconds, R.T.) (GHS316. Sigma-Aldrich) dehydrated, and mounted with SecureMount (Fisher HealthCare™ PROTOCOL™ Mounting Media. #022-208. Fisher Scientific. Thermofisher Scientific) . Scoring index was determined by scoring the percentage of positive cells on a scale of 0 to 3 as well as the intensity of ZIP9 staining on a scale of 0 to 4 (1=1-25%, 2=26-50%, 3=51-75%, 4=76-100%).

The staining of the tissue microarrays (ME1004h) for AR detection was performed by University of Pennsylvania Pathology Clinical Service Center—Anatomic Pathology Division, using the highest grade, CLIA (Clinical Laboratory Improvement Amendments) certified and validated test available. Briefly, five-micron sections of formalin-fixed paraffin-embedded tissue were stained using antibody against Androgen Receptor [(Leica AR-318-L-CE, clone AR27 (clone AR27, 1:25)]. Staining was done on a Leica Bond-III™ instrument using the Bond Polymer Refine Detection System (Leica Microsystems DS9800). Heat-induced epitope retrieval was done for 20 minutes with ER2 solution (Leica Microsystems AR9640). All the experiment was done at room temperature. Slides are washed three times between each step with bond wash buffer or water. The slides were reviewed and scored in blinded fashion by a board-certified U. Penn pathologist. Prostate tissue was used as the positive control.

Immunocytochemistry

To detect ZIP9 protein in WM46 isogenic clones cells were fixed in 4% PFA for 7 minutes. After two washes with PBS (5 min), cells were permeabilized with PBS/0.1% Triton X-100 for 1 minute at R.T. Cells were washed twice with PBS on a shaker. Once treated with 1.5% $H_2O_2$/PBS solution for 15 minutes (R.T.), cells were washed again and blocked with 5% BSA for one hour at R.T. For primary antibody incubation, α-ZIP9 antibody [(SLC39A9 Antibody (PAS-52485), Thermofisher Scientific, Waltham, MA)] was diluted 1:500 in 1% BSA and cells were incubated overnight at 4° C. After washing three times with PBS on a shaker, the slide was incubated with Biotinylated Secondary antibody (Vectastain Kit, Peroxidase Rabbit IgG, PK-4001) for one hour at R.T. Cells were washed three times with PBS, ABC reagent (prepared 30 minutes in advance) was added and samples were incubated for 30 minutes at R.T. After three washes with PBS, samples were incubated for 1.5 minutes with Vector Laboratories DAB Peroxidase (HRP) Substrate Kit (NC9276270. Vector laboratories, Burlingame, CA). Cells were counterstained with hematoxylin (10 seconds, R.T.) (GHS316. Sigma-Aldrich) and mounted with SecureMount (Fisher HealthCare™ PROTOCOL™ Mounting Media. #022-208. Thermofisher Scientific).

ENUMERATED EMBODIMENTS

The following exemplary embodiments are provided, the numbering of which is not to be construed as designating levels of importance:

Embodiment 1 provides a method of treating cancer, the method comprising: administering to a subject in need thereof a composition comprising a therapeutically effective amount of at least one active agent that inhibits ZIP9, and wherein the cancer is not androgen receptor (AR)-dependent.

Embodiment 2 provides the method of embodiment 1, wherein the cancer does not express AR.

Embodiment 3 provides the method of any one of embodiments 1-2, wherein any AR expressed in the cancer does not have significant functional effect on the cancer.

Embodiment 4 provides the method of any one of embodiments 1-3, wherein the cancer is not prostate cancer and/or the cancer is not testicular cancer.

Embodiment 5 provides the method of any of embodiments 1-4, wherein the cancer is not prostate or testicular cancer, and wherein the cancer is selected from the group consisting of squamous-cell carcinoma, basal cell carcinoma, adenocarcinoma, hepatocellular carcinomas, renal cell carcinomas, pancreatic cancer, stomach cancer, liver cancer, colon cancer, bladder cancer, bowel cancer, kidney cancer, lung cancer, head and neck cancer, stomach cancer, leukemias, benign or malignant lymphomas, benign or malignant melanomas, myeloproliferative diseases, sarcomas, thyroid cancer, astrocytoma, esophageal cancer, carcinosarcoma, Hodgkin's disease, Wilms' tumor, and teratocarcinomas.

Embodiment 6 provides the method of any one of embodiments 1-4, wherein the cancer is benign or malignant melanoma.

Embodiment 7 provides the method of any one of embodiments 1-4, wherein the cancer is pancreatic ductal adenocarcinoma (PDAC).

Embodiment 8 provides the method of any one of embodiments 1-7, wherein the at least one active agent is bicalutamide, enzalutamide, flutamide, nilutamide, apalutamide (ARN-509), darolutamide (ODM-201), ralaniten (EPI-001), or dimethylcurcumin (ASC-J9).

Embodiment 9 provides the method of any one of embodiments 1-8, further comprising administering an additional therapeutic agent to the subject.

Embodiment 10 provides the method of any one of embodiments 1-9, wherein the additional therapeutic agent is administered sequentially or concurrently with the at least one active agent to the subject.

Embodiment 11 provides the method of any one of embodiments 1-10, wherein the additional therapeutic agent is selected from the group consisting of a chemotherapeutic agent and radiation.

Embodiment 12 provides the method of any one of embodiments 1-11, wherein the subject is male.

Embodiment 13 provides the method of any one of embodiments 1-12, wherein the cancer comprises a plurality of cancerous cells, and wherein the cancerous cells do not have detectable levels of AR as measured by immunohistochemistry.

Embodiment 14 provides the method of any one of embodiments 1-13, wherein tumor proliferation is selectively reduced in a male subject compared to a female subject.

Embodiment 15 provides the method of any one of embodiments 1-14, wherein the at least one active agent is administered at a lower dose than the lowest standard dose of the at least one active agent for treating a cancer that is androgen receptor (AR)-dependent.

Embodiment 16 provides a method of treating cancer, the method comprising: identifying a subject suffering from cancer that has failed at least one prior cancer therapy, wherein the cancer is not androgen receptor (AR)-dependent; and administering to the subject a composition comprising a therapeutically effective amount of at least one active agent that inhibits ZIP9.

Embodiment 17 provides a method of reducing proliferation of cells in a cancerous tumor, the method comprising: contacting cells in the cancerous tumor with at least one active agent that inhibits ZIP9; and reducing the proliferation of cells in the cancerous tumor, wherein the cancerous tumor is not AR-dependent; and wherein the cancerous tumor is not prostate cancer or testicular cancer.

Embodiment 18 provides the method of embodiment 17, wherein the cancerous tumor is melanoma.

Embodiment 19 provides the method of any one of embodiments 17-18, wherein the cancerous tumor is pancreatic ductal adenocarcinoma (PDAC).

Embodiment 20 provides the method of any one of embodiments 17-19, wherein the at least one active agent is bicalutamide, enzalutamide, flutamide, nilutamide, apalutamide (ARN-509), darolutamide (ODM-201), ralaniten (EPI-001), or dimethylcurcumin (ASC-J9).

Embodiment 21 provides the method of any one of embodiments 17-20, further comprising exposing cells in the cancerous tumor with an additional therapeutic agent.

Embodiment 22 provides the method of any one of embodiments 17-21, wherein the exposing is sequential or concurrent with the contacting with the at least one active agent.

Embodiment 23 provides the method of any one of embodiments 17-22, wherein the additional therapeutic agent is selected from the group consisting of a chemotherapeutic agent and radiation.

Embodiment 24 provides the method of any one of embodiments 17-23, wherein the cells are male mammal cells.

Embodiment 25 provides the method of any one of embodiments 17-24, wherein the mammal is human.

Embodiment 26 provides a method of treating cancer, the method comprising: administering to a subject in need thereof a composition comprising a therapeutically effective amount of at least one active agent that inhibits ZIPS, and wherein the cancer is not prostate cancer and/or the cancer is not testicular cancer.

Embodiment 27 provides the method of embodiment 26, wherein the cancer is selected from the group consisting of squamous-cell carcinoma, basal cell carcinoma, adenocarcinoma, hepatocellular carcinomas, renal cell carcinomas, pancreatic cancer, stomach cancer, liver cancer, colon cancer, bladder cancer, bowel cancer, kidney cancer, lung cancer, head and neck cancer, stomach cancer, leukemias, benign or malignant lymphomas, benign or malignant melanomas, myeloproliferative diseases, sarcomas, thyroid cancer, astrocytoma, esophageal cancer, carcinosarcoma, Hodgkin's disease, Wilms' tumor, and teratocarcinomas.

Embodiment 28 provides the method of any one of embodiments 26-27, wherein the cancer is benign or malignant melanoma.

Embodiment 29 provides the method of any one of embodiments 26-27, wherein the pancreatic cancer is pancreatic ductal adenocarcinoma (PDAC).

Embodiment 30 provides the method of any one of embodiments 26-29, wherein the at least one active agent is bicalutamide, enzalutamide, flutamide, nilutamide, apalutamide (ARN-509), darolutamide (ODM-201), ralaniten (EPI-001), or dimethylcurcumin (ASC-J9).

Embodiment 31 provides the method of any one of embodiments 26-30, further comprising administering an additional therapeutic agent to the subject.

Embodiment 32 provides the method of any one of embodiments 26-31, wherein the additional therapeutic agent is administered sequentially or concurrently with the at least one active agent to the subject.

Embodiment 33 provides the method of any one of embodiments 26-32, wherein the additional therapeutic agent is selected from the group consisting of a chemotherapeutic agent and radiation.

Embodiment 34 provides the method of any one of embodiments 26-33, wherein the subject is male.

Embodiment 35 provides the method of any one of embodiments 26-34, wherein the subject is human.

What is claimed is:

1. A method of treating or ameliorating cancer, the method comprising:
    administering to a subject in need thereof a composition comprising a therapeutically effective amount of at least one active agent that inhibits ZIP9,
    wherein the at least one active agent is bicalutamide, enzalutamide, flutamide, nilutamide, apalutamide (ARN-509), darolutamide (ODM-201), ralaniten (EPI-001), or dimethylcurcumin (ASC-J9);
    wherein the cancer is selected from the group consisting of squamous-cell carcinoma, basal cell carcinoma, adenocarcinoma, hepatocellular carcinomas, renal cell carcinomas, pancreatic cancer, liver cancer, colon cancer, bladder cancer, bowel cancer, kidney cancer, lung cancer, head and neck cancer, stomach cancer, leukemias, benign or malignant lymphomas, benign or malignant melanomas, myeloproliferative diseases, sarcomas, thyroid cancer, astrocytoma, esophageal cancer, carcinosarcoma, Hodgkin's disease, Wilms' tumor, and teratocarcinomas; and
    wherein cancerous cells in the cancer do not have detectable levels of androgen receptor (AR) as measured by immunohistochemistry relative to a known AR-expressing and AR-responsive tumor.

2. The method of claim 1, wherein the cancer is benign or malignant melanoma.

3. The method of claim 1, wherein the pancreatic cancer is pancreatic ductal adenocarcinoma (PDAC).

4. The method of claim 1, further comprising administering an additional therapeutic agent to the subject.

5. The method of claim 4, wherein the additional therapeutic agent is administered sequentially or concurrently with the at least one active agent to the subject.

6. The method of claim 4, wherein the additional therapeutic agent is selected from the group consisting of a chemotherapeutic agent and radiation.

7. The method of claim 1, wherein the subject is male.

8. The method of claim 1, wherein the at least one active agent is administered at a lower dose than the lowest standard dose of the at least one active agent for treating a cancer that expresses AR.

9. A method of treating or ameliorating cancer, the method comprising:
    identifying a subject suffering from cancer that has failed at least one prior cancer therapy, wherein cancerous cells in the cancer do not have detectable levels of androgen receptor (AR) as measured by immunohistochemistry relative to a known AR-expressing and AR-responsive tumor; wherein the cancer is selected from the group consisting of squamous-cell carcinoma, basal cell carcinoma, adenocarcinoma, hepatocellular carcinomas, renal cell carcinomas, pancreatic cancer, liver cancer, colon cancer, bladder cancer, bowel cancer, kidney cancer, lung cancer, head and neck cancer, stomach cancer, leukemias, benign or malignant lymphomas, benign or malignant melanomas, myeloproliferative diseases, sarcomas, thyroid cancer, astrocytoma, esophageal cancer, carcinosarcoma, Hodgkin's disease, Wilms' tumor, and teratocarcinomas; and administering to the subject a composition comprising a therapeutically effective amount of at least one active agent that inhibits ZIP9, wherein the at least one active agent is bicalutamide, enzalutamide, flutamide, nilutamide, apalutamide (ARN-509), darolutamide (ODM-201), ralaniten (EPI-001), or dimethylcurcumin (ASC-J9).

10. A method of reducing proliferation of cells in a cancerous tumor, the method comprising:

contacting cells in the cancerous tumor with at least one active agent that inhibits ZIP9, wherein the at least one active agent is bicalutamide, enzalutamide, flutamide, nilutamide, apalutamide (ARN-509), darolutamide (ODM-201), ralaniten (EPI-001), or dimethylcurcumin (ASC-J9); and reducing the proliferation of cells in the cancerous tumor, wherein the cells in the cancerous tumor do not have detectable levels of androgen receptor (AR) as measured by immunohistochemistry relative to a known AR expressing and AR responsive tumor; and wherein the cancer is selected from the group consisting of squamous-cell carcinoma, basal cell carcinoma, adenocarcinoma, hepatocellular carcinomas, renal cell carcinomas, pancreatic cancer, liver cancer, colon cancer, bladder cancer, bowel cancer, kidney cancer, lung cancer, head and neck cancer, stomach cancer, leukemias, benign or malignant lymphomas, benign or malignant melanomas, myeloproliferative diseases, sarcomas, thyroid cancer, astrocytoma, esophageal cancer, carcinosarcoma, Hodgkin's disease, Wilms' tumor, and teratocarcinomas.

11. The method of claim 10, wherein the cancerous tumor is melanoma.

12. The method of claim 10, wherein the cancerous tumor is pancreatic ductal adenocarcinoma (PDAC).

13. The method of claim 10, further comprising exposing cells in the cancerous tumor with an additional therapeutic agent.

14. The method of claim 13, wherein the exposing is sequential or concurrent with the contacting with the at least one active agent.

15. The method of claim 14, wherein the additional therapeutic agent is selected from the group consisting of a chemotherapeutic agent and radiation.

16. The method of claim 10, wherein the cells are male mammal cells.

17. The method of claim 16, wherein the mammal is human.

18. A method of treating or ameliorating cancer, the method comprising:

administering to a subject in need thereof a composition comprising a therapeutically effective amount of at least one active agent that inhibits ZIP9, wherein the at least one active agent is bicalutamide, enzalutamide, flutamide, nilutamide, apalutamide (ARN-509), darolutamide (ODM-201), ralaniten (EPI-001), or dimethylcurcumin (ASC-J9), wherein cells in the cancer do not have detectable levels of androgen receptor (AR) as measured by immunohistochemistry relative to a known AR expressing and AR responsive tumor; and wherein the cancer is selected from the group consisting of squamous-cell carcinoma, basal cell carcinoma, adenocarcinoma, hepatocellular carcinomas, renal cell carcinomas, pancreatic cancer, liver cancer, colon cancer, bladder cancer, bowel cancer, kidney cancer, lung cancer, head and neck cancer, stomach cancer, leukemias, benign or malignant lymphomas, benign or malignant melanomas, myeloproliferative diseases, sarcomas, thyroid cancer, astrocytoma, esophageal cancer, carcinosarcoma, Hodgkin's disease, Wilms' tumor, and teratocarcinomas.

19. The method of claim 18, wherein the cancer is benign or malignant melanoma.

20. The method of claim 18, wherein the pancreatic cancer is pancreatic ductal adenocarcinoma (PDAC).

21. The method of claim 18, further comprising administering an additional therapeutic agent to the subject.

22. The method of claim 21, wherein the additional therapeutic agent is administered sequentially or concurrently with the at least one active agent to the subject.

23. The method of claim 22, wherein the additional therapeutic agent is selected from the group consisting of a chemotherapeutic agent and radiation.

24. The method of claim 18, wherein the subject is male.

25. The method of claim 24, wherein the subject is human.

* * * * *